(12) United States Patent
Millerd et al.

(10) Patent No.: US 8,747,361 B2
(45) Date of Patent: *Jun. 10, 2014

(54) SAFETY CATHETER

(75) Inventors: Don Millerd, San Diego, CA (US); Hooman Asbaghi, San Diego, CA (US)

(73) Assignee: Milaghi Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,914

(22) Filed: Jul. 9, 2012

(65) Prior Publication Data

US 2012/0283641 A1    Nov. 8, 2012

Related U.S. Application Data

(63) Continuation of application No. 12/874,200, filed on Sep. 1, 2010, now Pat. No. 8,216,188, which is a continuation-in-part of application No. 12/494,108, filed on Jun. 29, 2009, now Pat. No. 8,216,187.

(51) Int. Cl.
*A61M 5/178* (2006.01)

(52) U.S. Cl.
USPC .................................................. 604/164.12

(58) Field of Classification Search
USPC ........................................ 604/164.01, 164.12
See application file for complete search history.

(56) References Cited

U.S. PATENT DOCUMENTS

| | | | | |
|---|---|---|---|---|
| 4,723,946 A | * | 2/1988 | Kay | 604/267 |
| 5,053,014 A | * | 10/1991 | Van Heugten | 604/167.03 |
| 5,104,384 A | * | 4/1992 | Parry | 604/192 |
| 5,205,829 A | * | 4/1993 | Lituchy | 604/164.08 |
| 5,267,972 A | * | 12/1993 | Anderson | 604/192 |
| 5,292,314 A | * | 3/1994 | D'Alessio et al. | 604/198 |
| 5,376,080 A | * | 12/1994 | Petrussa | 604/198 |
| 5,389,085 A | * | 2/1995 | D'Alessio et al. | 604/198 |
| 5,403,283 A | * | 4/1995 | Luther | 604/288.02 |
| 5,403,286 A | * | 4/1995 | Lockwood, Jr. | 604/110 |
| 5,501,675 A | * | 3/1996 | Erskine | 604/263 |
| 5,562,629 A | * | 10/1996 | Haughton et al. | 604/158 |
| 5,562,634 A | | 10/1996 | Flumene | |

(Continued)

FOREIGN PATENT DOCUMENTS

| | | |
|---|---|---|
| EP | 0830872 | 3/1998 |
| EP | 0847289 | 6/1998 |

(Continued)

OTHER PUBLICATIONS

U.S. Appl. No. 12/494,108, NF OA mailed Dec. 27, 2010, 8 pages Dec. 27, 2010.

(Continued)

*Primary Examiner* — Aarti B Berdichevsky
(74) *Attorney, Agent, or Firm* — John V. Daniluck; Bingham Greenebaum Doll LLP

(57) ABSTRACT

A device and method for positioning a catheter to establish a fluid access site into the vasculature of a patient includes a luer assembly having a cannula or catheter, a shuttle assembly having a stylet for stiffening the catheter, and a holder assembly having an actuator for providing controlled retraction into a handle. The safety catheter comprises a flash window that allows a clinician to view when the vasculature of a patient has been properly accessed and to confirm that the stylet has been fully retracted into a safe position.

6 Claims, 31 Drawing Sheets

(56) References Cited

U.S. PATENT DOCUMENTS

| | | | | |
|---|---|---|---|---|
| 5,578,011 | A * | 11/1996 | Shaw | 604/110 |
| 5,683,368 | A * | 11/1997 | Schmidt | 604/164.01 |
| 5,700,250 | A * | 12/1997 | Erskine | 604/263 |
| 5,713,876 | A * | 2/1998 | Bogert et al. | 604/243 |
| 5,800,395 | A * | 9/1998 | Botich et al. | 604/110 |
| 5,817,058 | A * | 10/1998 | Shaw | 604/110 |
| 5,853,393 | A * | 12/1998 | Bogert | 604/165.02 |
| 5,935,102 | A * | 8/1999 | Bowden et al. | 604/95.04 |
| 5,989,220 | A * | 11/1999 | Shaw et al. | 604/110 |
| 6,050,976 | A * | 4/2000 | Thorne et al. | 604/164.01 |
| 6,436,070 | B1 * | 8/2002 | Botich et al. | 604/110 |
| 6,475,189 | B1 * | 11/2002 | Lilley, Jr. | 604/164.01 |
| 6,530,905 | B2 * | 3/2003 | Asbaghi | 604/198 |
| 6,582,402 | B1 * | 6/2003 | Erskine | 604/164.08 |
| 6,626,864 | B2 * | 9/2003 | Jansen et al. | 604/110 |
| 6,726,658 | B2 * | 4/2004 | Hochman | 604/164.08 |
| 6,958,054 | B2 * | 10/2005 | Fitzgerald | 604/162 |
| 6,972,002 | B2 * | 12/2005 | Thorne | 604/164.08 |
| 7,125,396 | B2 * | 10/2006 | Leinsing et al. | 604/167.03 |
| 7,198,617 | B2 * | 4/2007 | Millerd | 604/192 |
| 7,229,421 | B2 * | 6/2007 | Jen et al. | 600/585 |
| 7,344,516 | B2 * | 3/2008 | Erskine | 604/110 |
| 7,422,572 | B2 * | 9/2008 | Popov et al. | 604/198 |
| 7,604,616 | B2 * | 10/2009 | Thoresen et al. | 604/164.08 |
| 7,618,396 | B2 * | 11/2009 | Slate et al. | 604/136 |
| 7,736,340 | B2 * | 6/2010 | Harding et al. | 604/164.08 |
| 7,753,887 | B2 * | 7/2010 | Botich et al. | 604/164.12 |
| 7,887,549 | B2 * | 2/2011 | Wenderow et al. | 606/108 |
| 8,216,187 | B2 * | 7/2012 | Millerd et al. | 604/164.12 |
| 8,216,188 | B2 * | 7/2012 | Millerd et al. | 604/164.12 |
| 2003/0060760 | A1 * | 3/2003 | Botich et al. | 604/110 |
| 2003/0199827 | A1 | 10/2003 | Thorne | |
| 2004/0127854 | A1 | 7/2004 | Leinsing | |
| 2005/0015053 | A1 | 1/2005 | Parker | |
| 2005/0245875 | A1 * | 11/2005 | Restelli et al. | 604/164.01 |
| 2007/0083162 | A1 * | 4/2007 | O'Reagan et al. | 604/167.03 |
| 2009/0131872 | A1 * | 5/2009 | Popov | 604/164.08 |
| 2009/0177163 | A1 * | 7/2009 | King et al. | 604/167.03 |
| 2010/0210934 | A1 * | 8/2010 | Belson | 600/371 |
| 2010/0256558 | A1 * | 10/2010 | Olson et al. | 604/95.01 |
| 2010/0331781 | A1 * | 12/2010 | Millerd et al. | 604/164.08 |
| 2011/0166528 | A1 * | 7/2011 | Millerd et al. | 604/168.01 |

FOREIGN PATENT DOCUMENTS

| | | |
|---|---|---|
| EP | 1689468 | 8/2006 |
| EP | 2417996 | 2/2012 |
| JP | 09192230 | 7/1997 |
| WO | 0241932 | 5/2002 |
| WO | 2007098355 | 8/2007 |
| WO | 2008030999 | 3/2008 |
| WO | 2009154824 | 12/2009 |

OTHER PUBLICATIONS

Applicant Response, U.S. Appl. No. 12/494,108, filed 2/17/211, 10 pages Feb. 17, 2011.
U.S. Appl. No. 12/494,108, Final Action mailed May 13, 2011, 8 pages.
Applicant Response, U.S. Appl. No. 12/494,108, filed Jul. 25, 2011, 10 pages.
U.S. Appl. No. 12/494,108, NF OA mailed Oct. 19, 2011, 6 pages.
Applicant Response, U.S. Appl. No. 12/494,108, filed Dec. 21, 2011, 8 pages.
U.S. Appl. No. 12/494,108, Notice of Allowance mailed May 14, 2012, 8 pages.
PCT/US2010/036922, Search Report & Written Opinion dated Jul. 27, 2010, 11 pages.
China Patent Office, Serial No. 201080029225.X, Office Action dated Mar. 21, 2013, 4 pages.
Applicant Response, Serial No. 201080029225.X, filed Oct. 8, 2013, 6 pages.
EPO, Serial No. 10794525.5, Search Report and Examination Report dated Apr. 17, 2013, 10 pages.
Applicant Response, Serial No. 10794525.5, filed Nov. 14, 2013, 11 pages.
U.S. Appl. No. 12/874,200, NF OA mailed Oct. 19, 2011, 5 pages.
Applicant Response, U.S. Appl. No. 12/874,200, filed Dec. 21, 2011, 3 pages.
U.S. Appl. No. 12/874,200, Notice of Allowance dated May 15, 2012, 5 pages.
Serial No. PCT/US2011/049428, Search Report and Written Opinion dated Dec. 22, 2011, 9 pages.
EPO, Serial No. 11822406.2, Search Report and Examination Report dated Sep. 19, 2013, 11 pages.

* cited by examiner

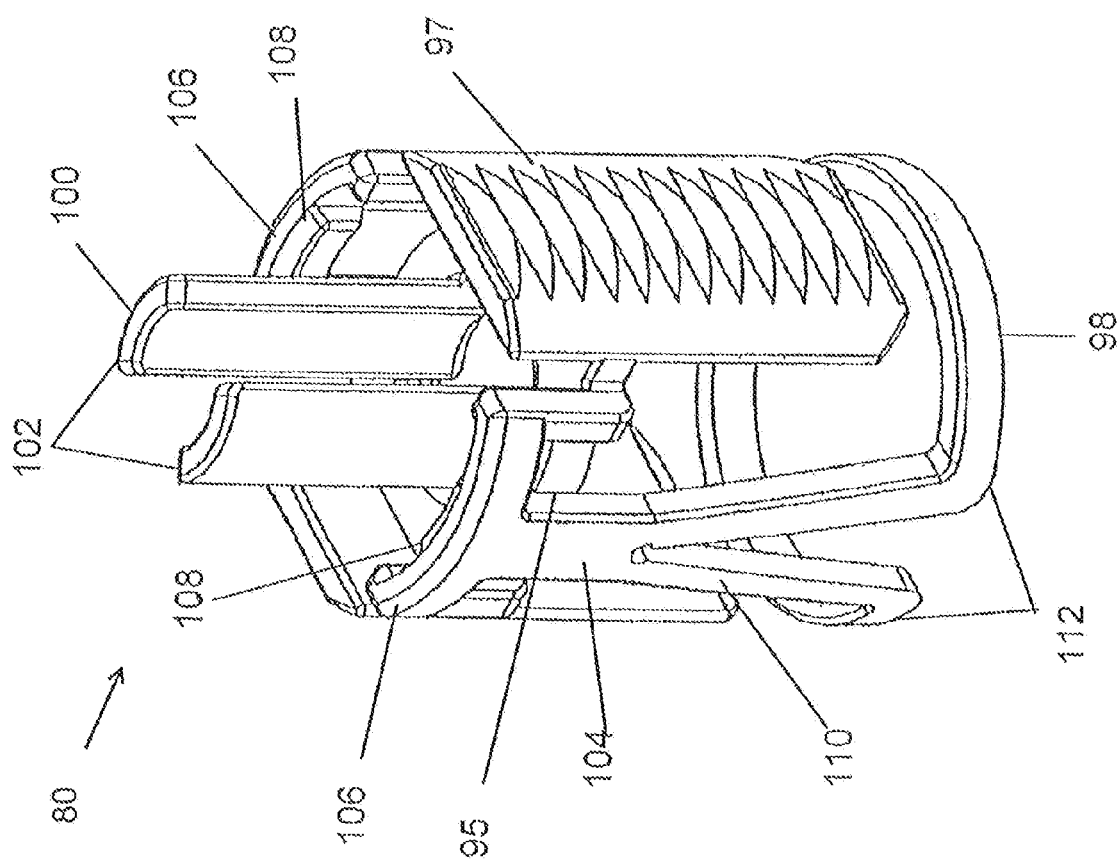

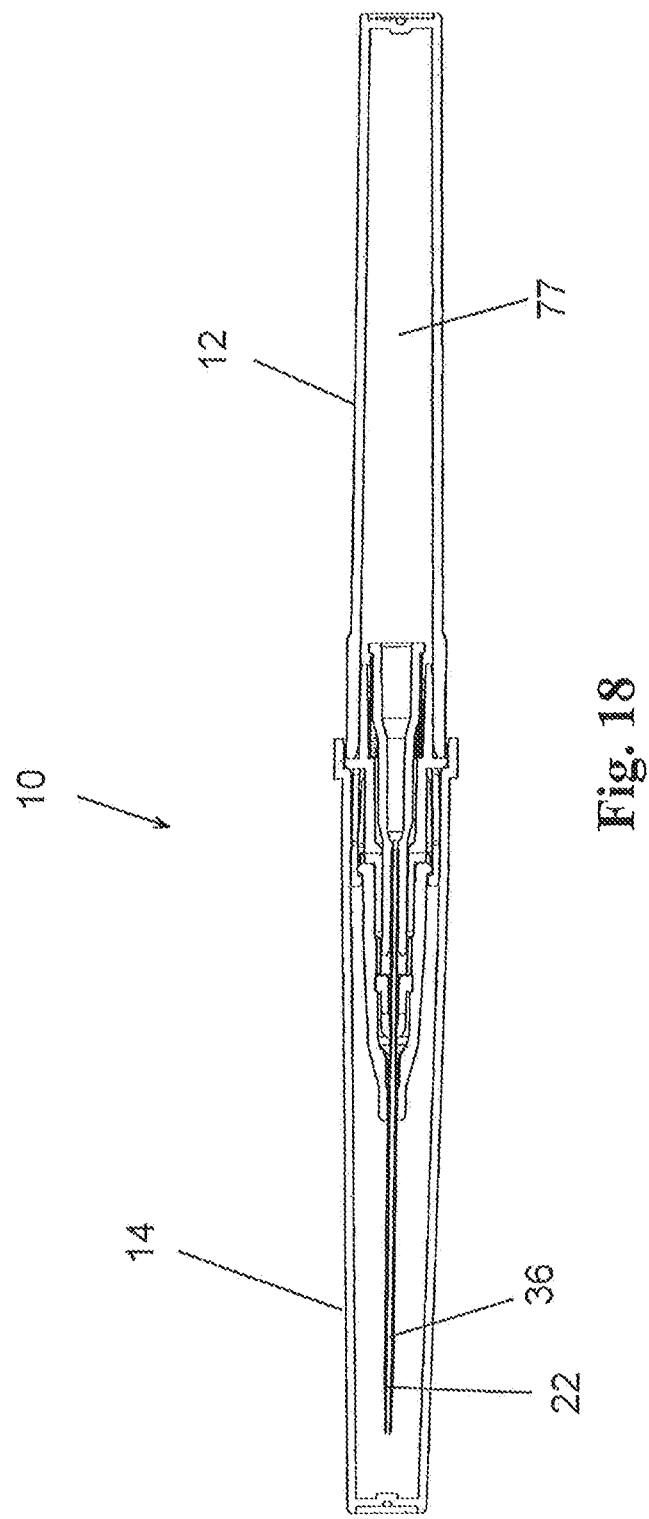

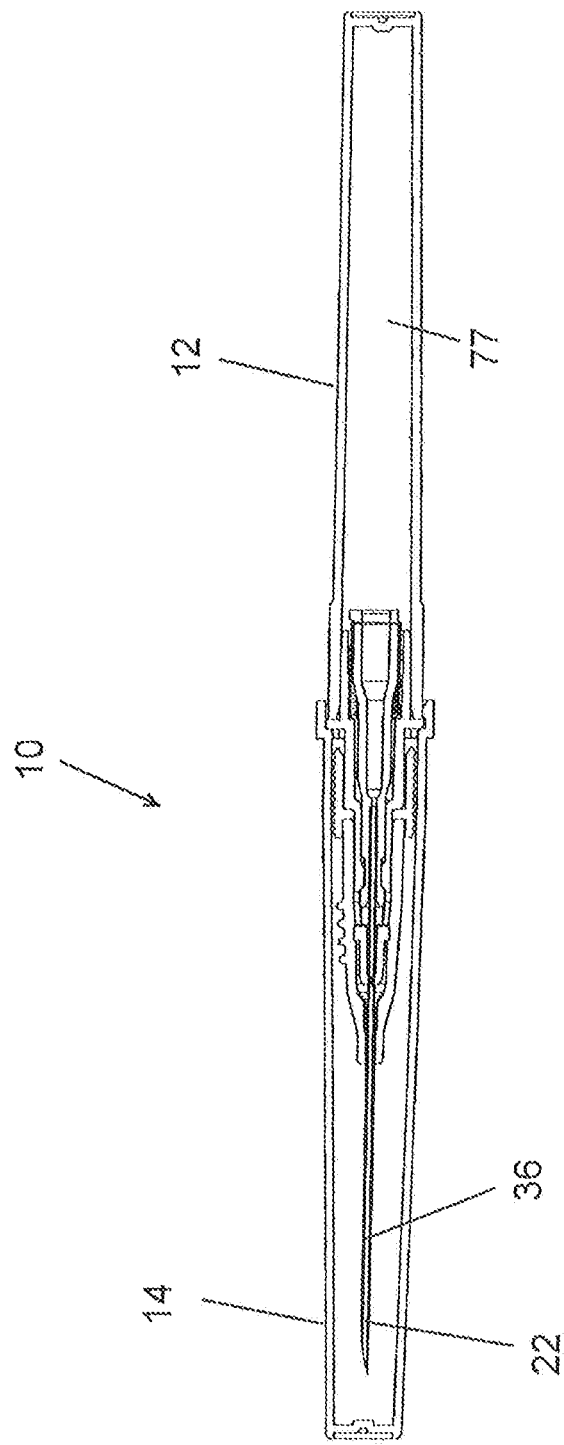

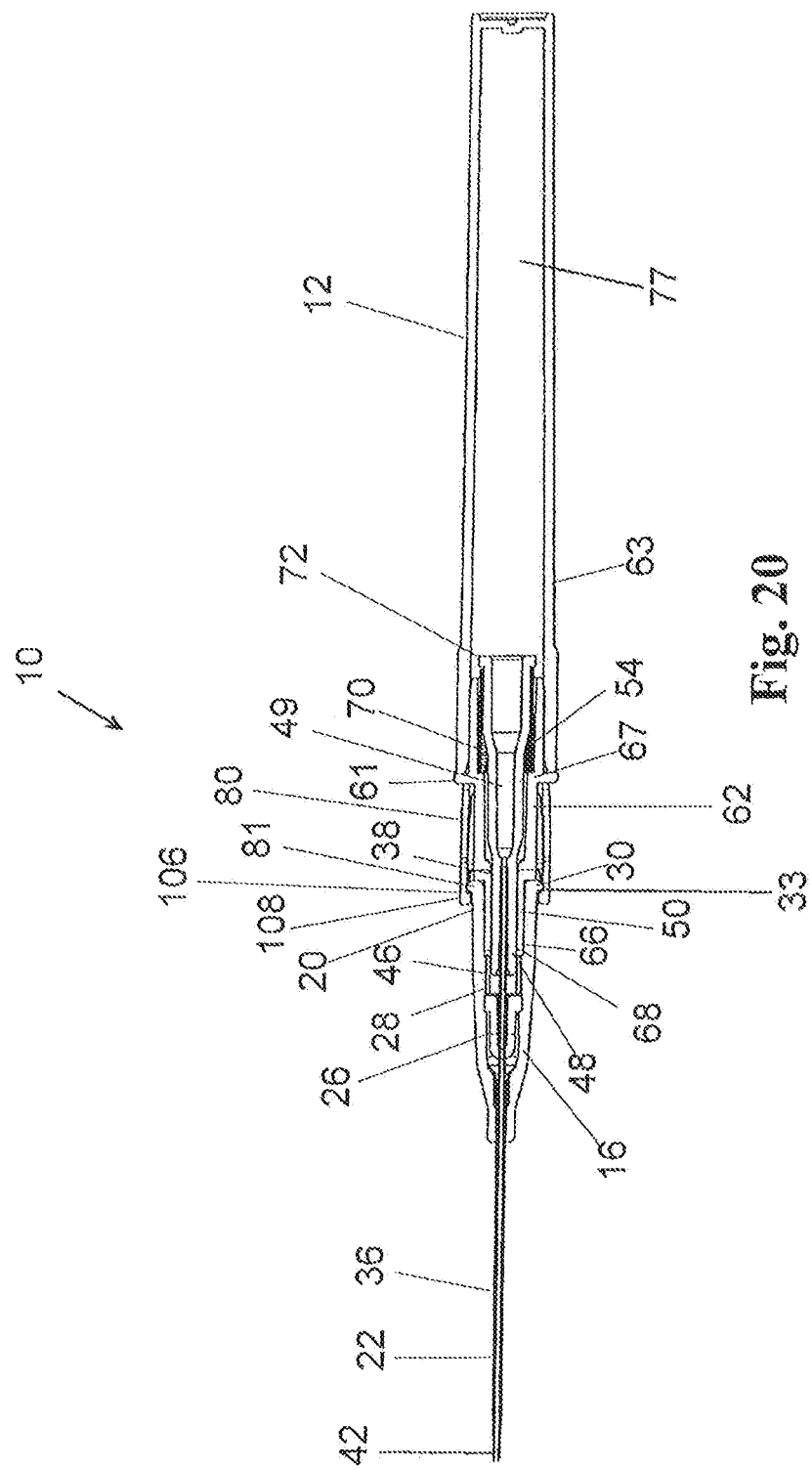

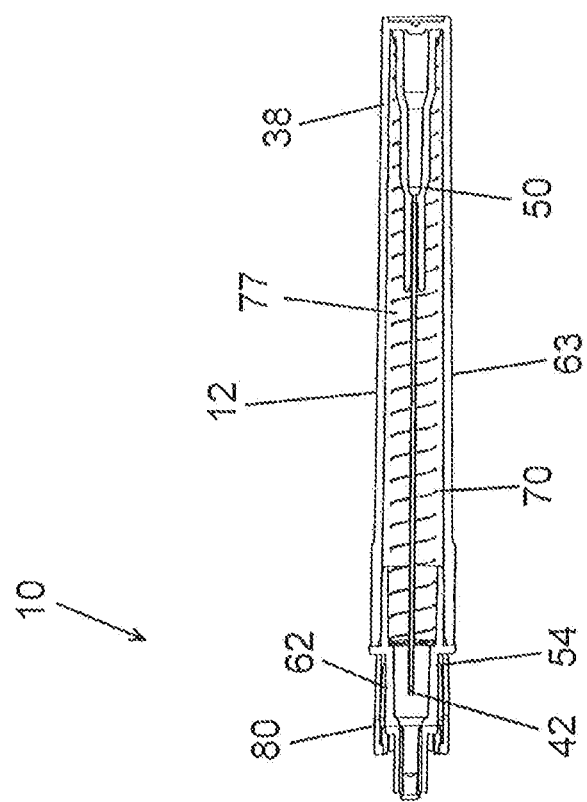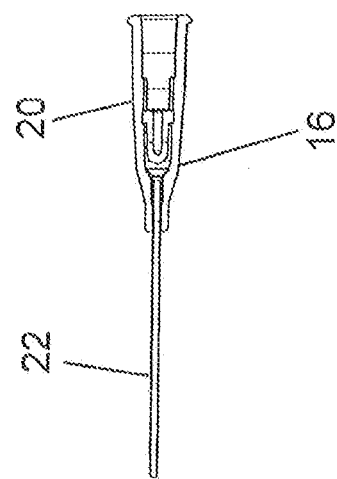
Fig. 26

SAFETY CATHETER

PRIORITY

This application is a continuation of application Ser. No. 12/874,200, filed Sep. 1, 2010, which is currently pending and which is a continuation-in-part of application Ser. No. 12/494,108 filed Jun. 29, 2009, which is currently pending. The contents of application Ser. Nos. 12/874,200 and 12/494,108 are incorporated herein by reference.

FIELD

Embodiments of the present invention relate in general, to medical catheters, and, in particular, to devices and methods of use relating to medical catheters having passive safety systems, controlled needle retraction, and visualization windows.

BACKGROUND

Fluid access into the vasculature of a patient may be necessary, or desirable, for any of several different reasons. When such access is desirable, a fluid flow path is generally established between an extracorporeal fluid source and the vasculature. Moreover, when an infusion protocol is involved that requires periodic injections, an established fluid access site that can be repetitively used for a sequence of different injections may be required. Establishing such an access site, however, can be problematic.

SUMMARY OF THE INVENTION

For the present invention, a safety catheter includes an actuator that interacts with a handle, a shuttle assembly, and a luer assembly. Together, these components cooperate with each other to position a flexible cannula, which is part of the luer assembly, in fluid communication with the vasculature of a patient. In this cooperation, the shuttle assembly interacts with the luer assembly so that a stylet, which is part of the shuttle assembly, stiffens the cannula during its insertion into the vasculature. Once the cannula (i.e. luer assembly) has been properly and effectively established in fluid communication with the vasculature, the stylet (i.e. shuttle assembly) may be safely withdrawn into a chamber that is formed inside the handle. As envisioned for the present invention, however, the actuator controls exactly when this withdrawal of the shuttle assembly and its stylet into the chamber is accomplished.

In a preferred embodiment of the safety catheter, the actuator is mounted on the handle of the safety catheter, and it is disposed for axial movement thereon between a proximal position and a distal position. Structurally, the actuator includes an annular shaped base member that is positioned on the handle and is centered on the longitudinal axis of the handle. It also has a pair of opposed rails that extend, in parallel, from the base member in a distal direction. Additionally, there is a pair of opposed living hinges on the actuator that are respectively positioned outwardly at a radial distance from the base member. Also, at this same radial distance from the base member, a pair of opposed arcuate bands interconnect the living hinges. Additionally, a dorsal pad is mounted on the base member.

During an assembly of the safety catheter, a plurality of resilient fingers that extend distally on the handle are engaged with the shuttle assembly. The luer assembly is then positioned to hold the fingers against the shuttle assembly. Specifically, the purpose of this engagement is to stationarily maintain the shuttle assembly in a distal position, relative to the chamber in the handle. Also, with this engagement, the stylet of the shuttle assembly is positioned in the cannula of the luer assembly to stiffen the cannula. Further, the actuator is positioned between the handle and the luer assembly, and it is substantially positioned over the shuttle assembly. In the assembly of the safety catheter, the actuator is located in its proximal position on the handle, and latches on the actuator grip the luer assembly to hold it on the shuttle assembly.

Operationally, once the stylet has been used to properly insert the flexible cannula of the luer assembly into the vasculature of the patient, the actuator is moved from its proximal position into its distal position. During this movement, several structural interactions occur simultaneously. For one, as the actuator is distally advanced, the latches release the luer assembly and the rails on the actuator push on the luer assembly to separate it from the shuttle assembly. For another, also during this advancement, the living hinges are compressed between stops on the handle to bias the actuator for a return back to its proximal position. Also, importantly, the base member itself urges against the resilient fingers of the handle to maintain their engagement with the shuttle assembly. This advancement of the actuator can continue until the arcuate bands that interconnect the living hinges make contact with stops on the handle to prevent any further distal advancement of the actuator.

When the actuator has been moved to its distal position, the luer assembly is effectively separated from the shuttle assembly. Nevertheless, the shuttle assembly and its stylet will remain distally extended from the catheter, and can still be manipulated by the handle, as long as the actuator is maintained in its distal position. This all changes, however, when the actuator is released. Upon a release of the actuator by the operator, the bias in the living hinges returns the actuator to its proximal position. This return of the actuator also releases the base member of the actuator from the resilient fingers on the handle. Thus, the fingers are no longer restrained by either the luer assembly or by the base member of the actuator. Consequently, when the actuator returns to its proximal position, the fingers on the handle release the shuttle assembly, and this causes the shuttle assembly to be withdrawn into the chamber of the handle by a spring drive.

BRIEF DESCRIPTION OF THE DRAWINGS

The accompanying drawings incorporated in and forming a part of the specification illustrate several aspects of the present disclosure, and together with the description serve to explain the principles of the invention; it being understood, however, that the described embodiments are not limited to the precise arrangements shown. In the drawings, like reference numerals refer to like elements in the several views. In the drawings:

FIG. 17 is a perspective view of the actuator shown in FIG. 2;

FIG. 18 is a side cross-section view of the safety catheter of FIG. 1 shown in a pre-use configuration with the shield in place;

FIG. 19 is a side cross-section view of the safety catheter of FIG. 18, shown rotated ninety degrees;

FIG. 20 is a side cross-section view of the safety catheter of FIG. 1, shown with the shield removed in a configuration for accessing the vasculature of a patient;

FIG. 26 is a side cross-section view of the safety catheter of FIG. 1, shown with the shuttle assembly retracted into the handle assembly;

DETAILED DESCRIPTION

Figure 1:
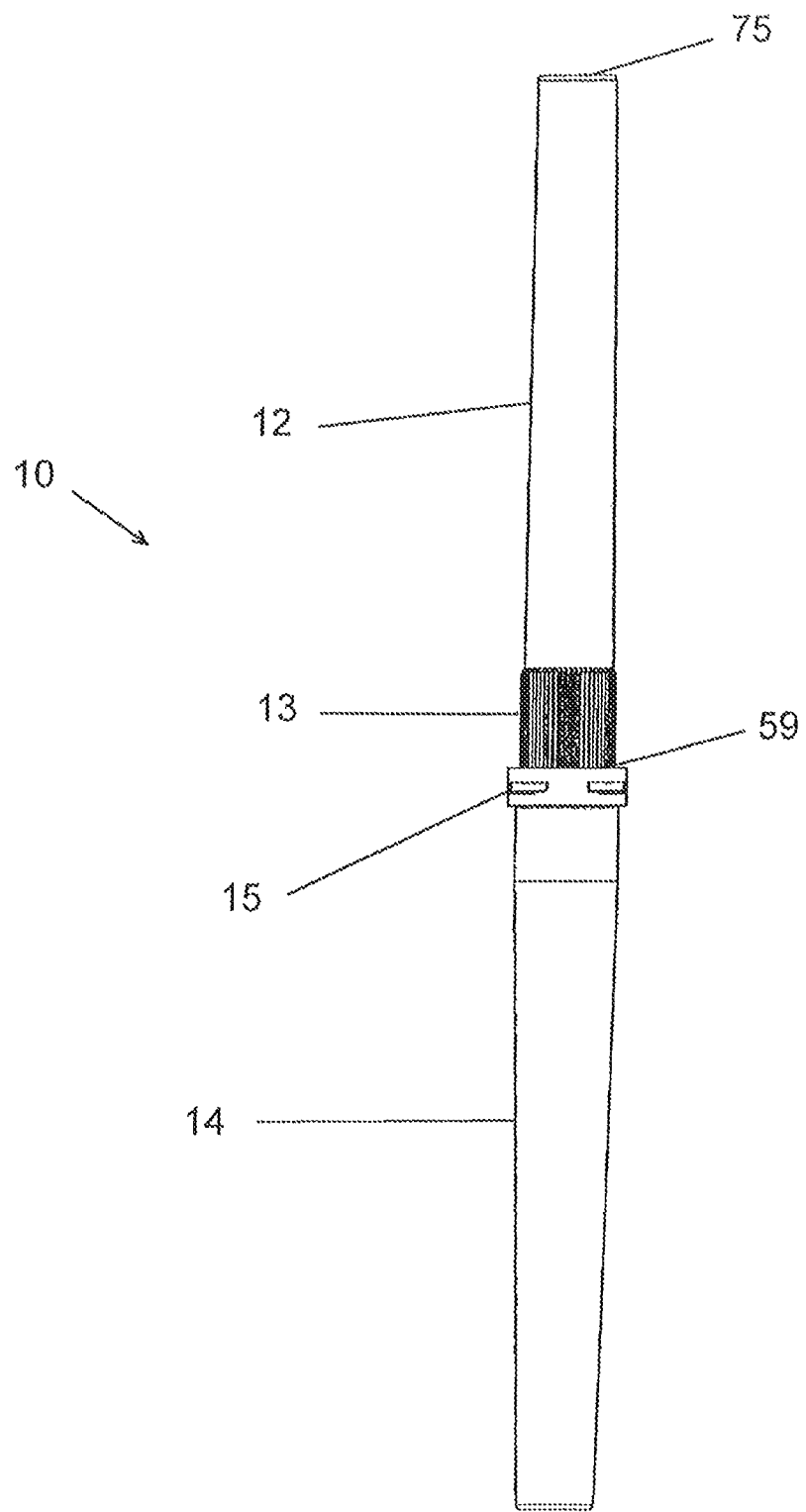
FIG. 1 is a side view of one version of a safety catheter shown with a shield engaged with a holder of the safety catheter.

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

As shown in the figures, versions illustrated herein may useful as a device for manipulating a stylet and/or any other stiffening or penetration element to position a catheter in fluid communication with the vasculature of a patient, and for subsequently concealing the stylet to prevent inadvertent "sticks" with the stylet. In one version, the retraction of the stylet or needle cannula is performed in a controlled manner, where controlled retraction may limit or mitigate tissue damage that can be associated with uncontrolled retraction that occurs automatically without input from a clinician.

When a catheter is used to establish a fluid access site into the vasculature of a patient, the catheter is generally flexible. Once positioned, a flexible cannula may be beneficial in reducing patient discomfort and in minimizing tissue damage. The flexible catheter, however, may need to be stiffened for insertion so that the distal end of the catheter, or cannula, can be passed through tissue and positioned in the vasculature. This stiffening can be accomplished, for example, by using a stylet that can be selectively inserted into the lumen of the catheter to stiffen the catheter during insertion. After the stiffened catheter has been properly positioned in the vasculature, the stylet can be removed from the catheter to leave the flexible catheter in fluid communication with the vasculature for delivery or removal of fluid therefrom.

Versions of the safety catheter described herein provide for a stylet or needle cannula that is passively retracted from a flexible catheter after the flexible catheter is properly positioned. Passively retracting the stylet after positioning the catheter may reduce the risk of accidental needle sticks by safely securing the stylet upon completion of the catheter insertion. In at least one version, a passive release refers to automatically releasing a needle or shuttle assembly for retraction. However, it will be appreciated that upon passive release, where a needle assembly is free to pass into a secured position, a user may still control the timing of the actual release to provide controlled retraction. Versions herein provide for the controlled retraction of the stylet after positioning the flexible catheter, where controlled retraction may allow the stylet to be safely secured without causing tissue damage that may be associated with an abrupt or uncontrolled retraction.

Versions described herein are directed to a catheter device and system that can be positioned to establish a single fluid access site for multiple infusions of a fluid medicament into the vasculature. The safety catheter system may be configured with a single-step operation such that the flexible catheter is separated from the stylet in an automated manner and the stylet is concealed after placement of the catheter to prevent accidental needlesticks and can include an actuator and/or other release device, mechanism, or component to facilitate controlled retraction.

Figure 2:
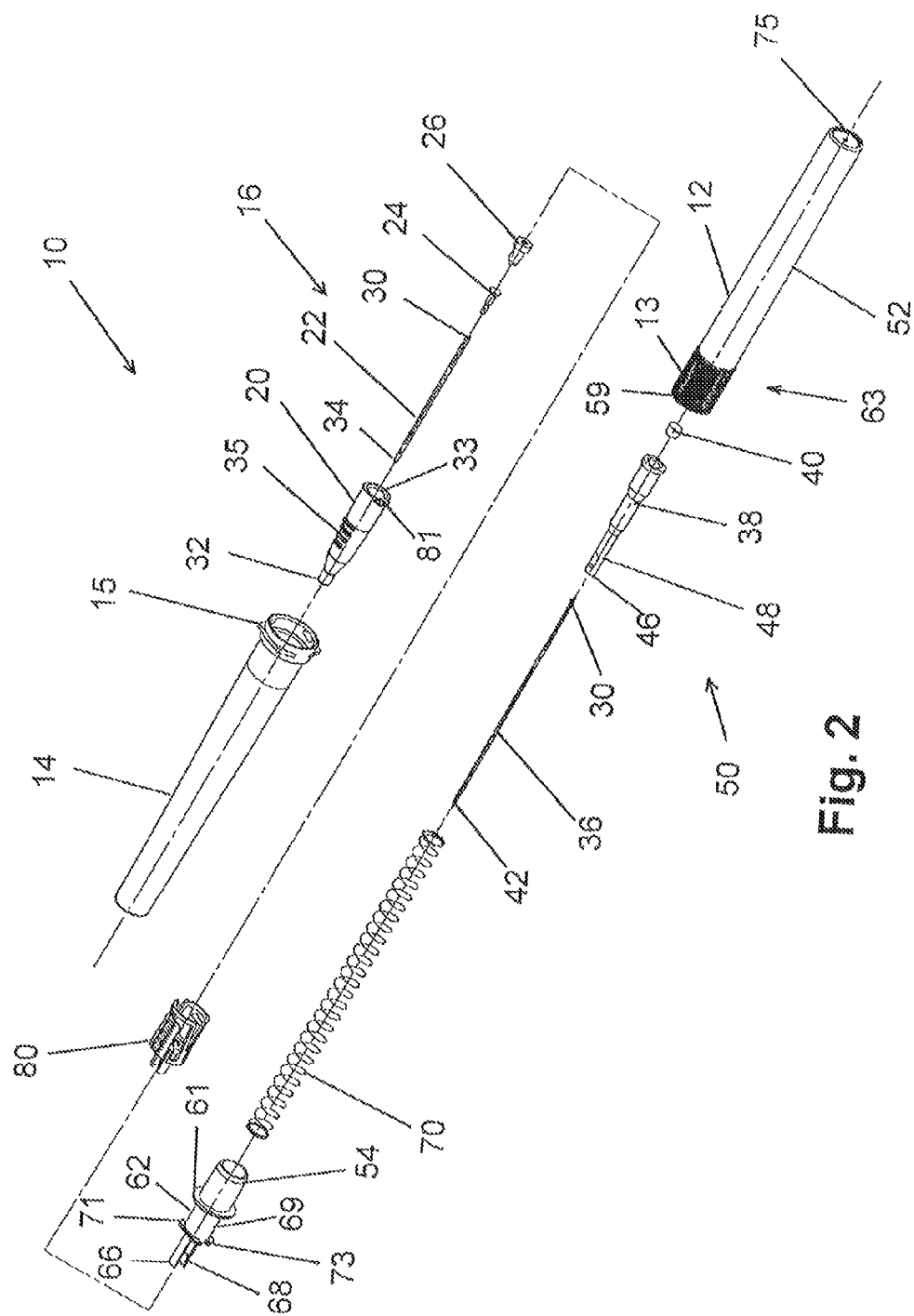
FIG. 2 is an exploded perspective view of the safety catheter of FIG. 1 having a luer assembly, a shuttle assembly, and a holder assembly.

Referring to FIGS. 1 and 2, one version of a safety catheter 10 is provided that is configured for insertion into the vasculature of a patient. The safety catheter 10 may be used to establish a single fluid access site into the vasculature of the patient that can be repetitively or sequentially used by extracorporeal fluid sources such as, but not limited to, a hypodermic syringe or IV pump (not shown). Generally, versions of the safety catheter 10 are configured to stiffen a flexible catheter or cannula 22 for insertion into the vasculature of a patient. Once the cannula 22 is properly positioned, the safety catheter 10 is configured to passively and/or automatically release a stylet 36, or any other suitable stiffening and/or penetration element, for withdrawal from the catheter. In one version, upon passive release of the stylet 36 from the cannula 22, the stylet 36 is configured for controlled retraction via an actuator 80 (FIG. 17) into a handle body 52 such that the sharp distal tip 42 of the stylet 36 is concealed to prevent accidental needlesticks. Controlled retraction of the stylet 36, after passive release from the cannula 22, may reduce or prevent tissue damage associated with an uncontrolled or abrupt retraction.

Figure 6:
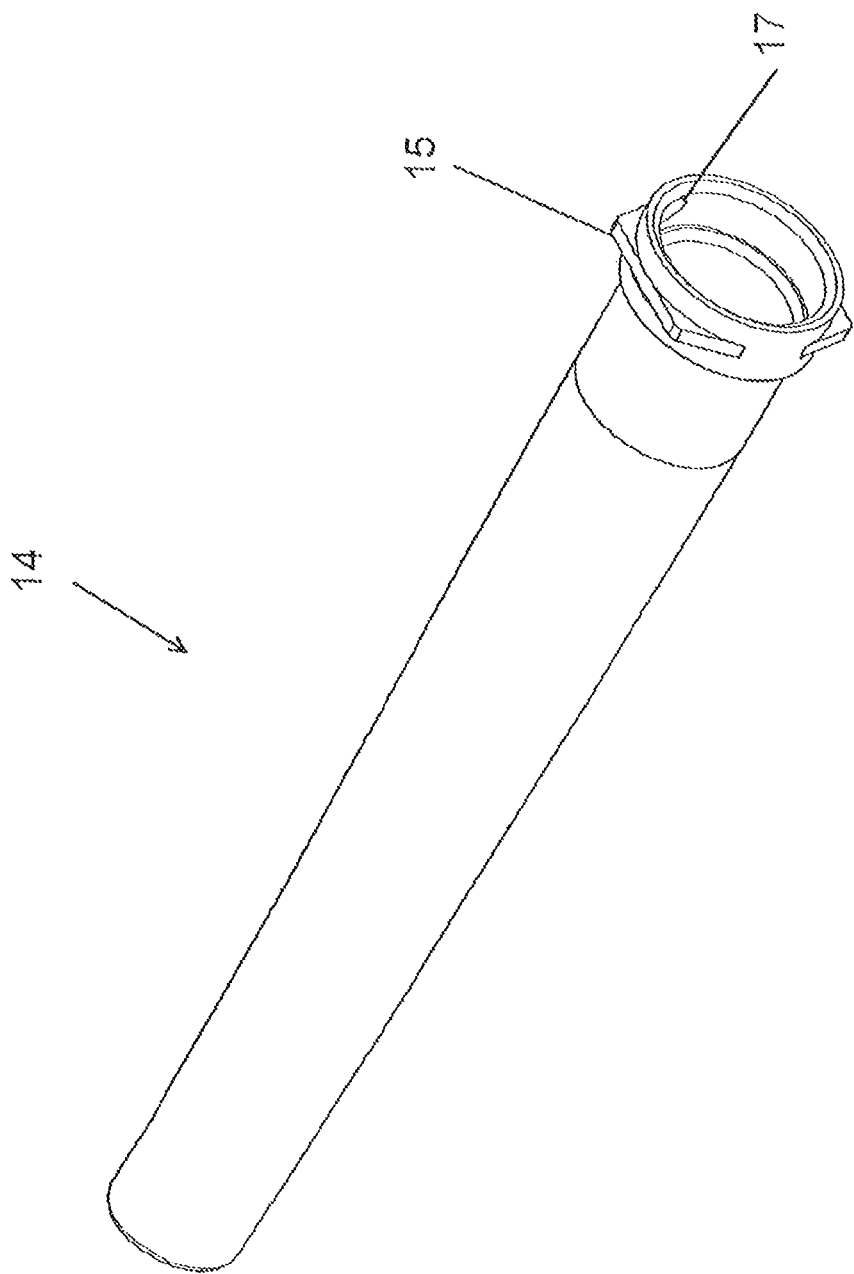
FIG. 6 is a perspective view of the shield shown in FIG. 2.

Referring to FIG. 1, one version of a safety catheter 10 is shown in a pre-deployment or pre-use configuration. More specifically, the safety catheter 10 is shown having a handle 12 with a textured surface 13 and a cap or shield 14. As illustrated, the shield 14 is engaged with the handle 12 to prevent exposure and contamination of the safety catheter 10. The shield 14 may have any suitable configuration designed to prevent exposure of the cannula 22 and stylet 36 (FIG. 2). Shield 14 comprises any suitable shape or grip and may be transparent or semitransparent to facilitate visualization of the cannula 22 and stylet 36. Referring to FIG. 6, the shield 14 may include flats 15 to prevent the safety catheter 10 from rolling on a flat surface and to facilitate automated engagement with the handle 12. The shield 14 may further include one or a plurality of projections 17, or any other suitable coupling, configured to engage the handle 12 to provide a secure coupling. The handle 12 may include any suitable corresponding coupling means.

Figure 7:
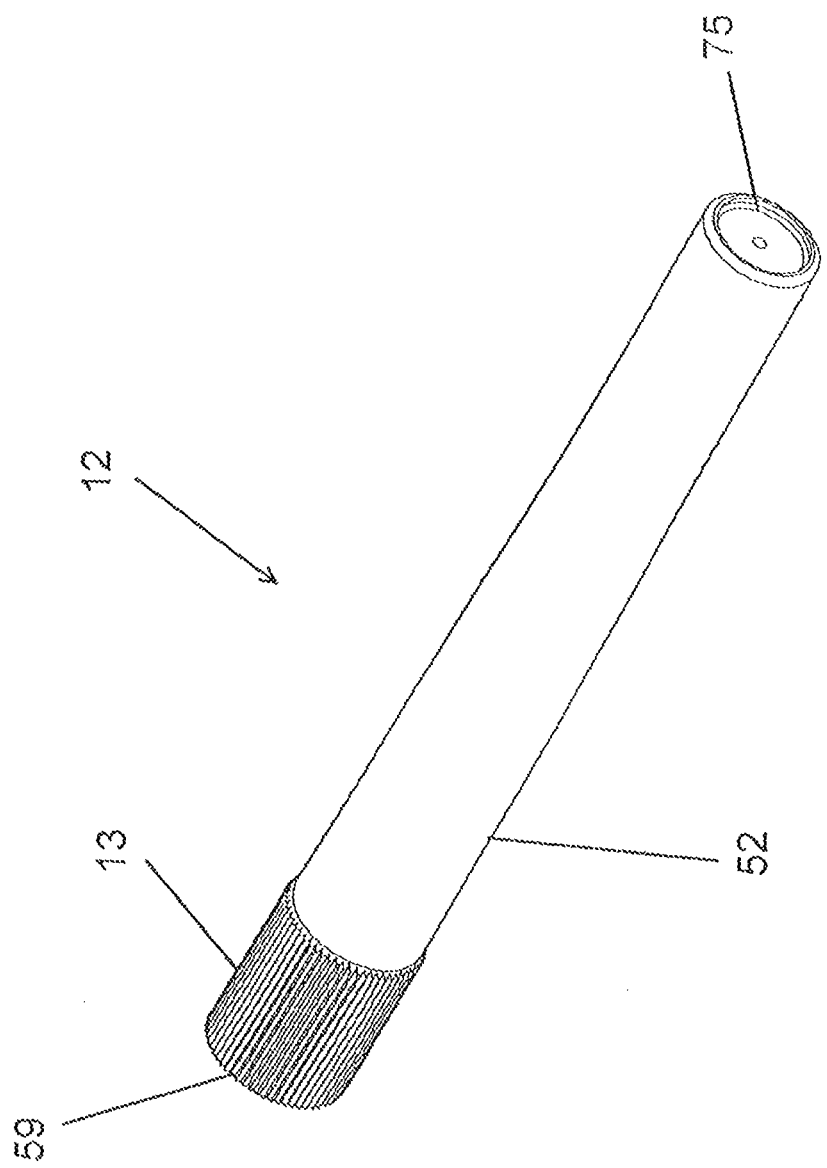
FIG. 7 is a perspective view of the holder shown in FIG. 2.

Referring to FIG. 7, the handle 12 may have any suitable gripping surface, such as textured surface 13, to facilitate handling, separation from the shield, operation, or the like. The handle 12 of the safety catheter, in one version, includes an elongated handle body 52 that has a proximal end 75 and a distal end 59. It is also formed with an internal chamber 77. During operation, after a catheter has been inserted into the vasculature of a patient, the handle body 52 is configured to retain the shuttle assembly 50 (FIG. 4) upon retraction of the stylet. The chamber 77 serves as a compartment for the stylet 36 to prevent accidental needlesticks and to prevent re-use.

In FIG. 1, the shield 14 is shown engaged with the handle 12, where any suitable coupling between the shield 14 and the handle, including a friction fit, a snap fit, a threaded fit, shrink wrap, tamper evident packaging, or the like, is contemplated. In one version, once the shield 14 is removed from the rest of the safety catheter 10 it cannot be reattached to the handle 12.

FIG. 2 illustrates an exploded view of the safety catheter 10 showing the various components of one version of the safety catheter 10. In addition to the shield 14, the safety catheter 10 includes a luer or hollow body portion 20, a cannula 22, an eyelet 24, and a one-way valve 26. In combination, these components comprise the luer assembly 16, which is shown and described in more detail with reference to FIG. 3. The safety catheter 10 further comprises a shuttle body assembly 50 including a stylet 36, a filter plug 40, and a shuttle body 38, which is shown in more detail in FIG. 4. FIG. 2 further illustrates an exploded view of a handle assembly 63 comprising a body top 54 engaged with a handle body 52 configured to retain a spring 70 therein. The handle assembly 63 further comprises an actuator 80 that is retained on the body top 54 and is configured for longitudinal movement relative thereto. In the illustrated version, the luer assembly 16, the shuttle assembly 50, and the handle assembly 63 interact with one another in multiple stages to provide a method of accurately and effectively accessing the vasculature of a patient and reducing the risk of accidental needlesticks after the vasculature has been properly accessed.

Figure 3:
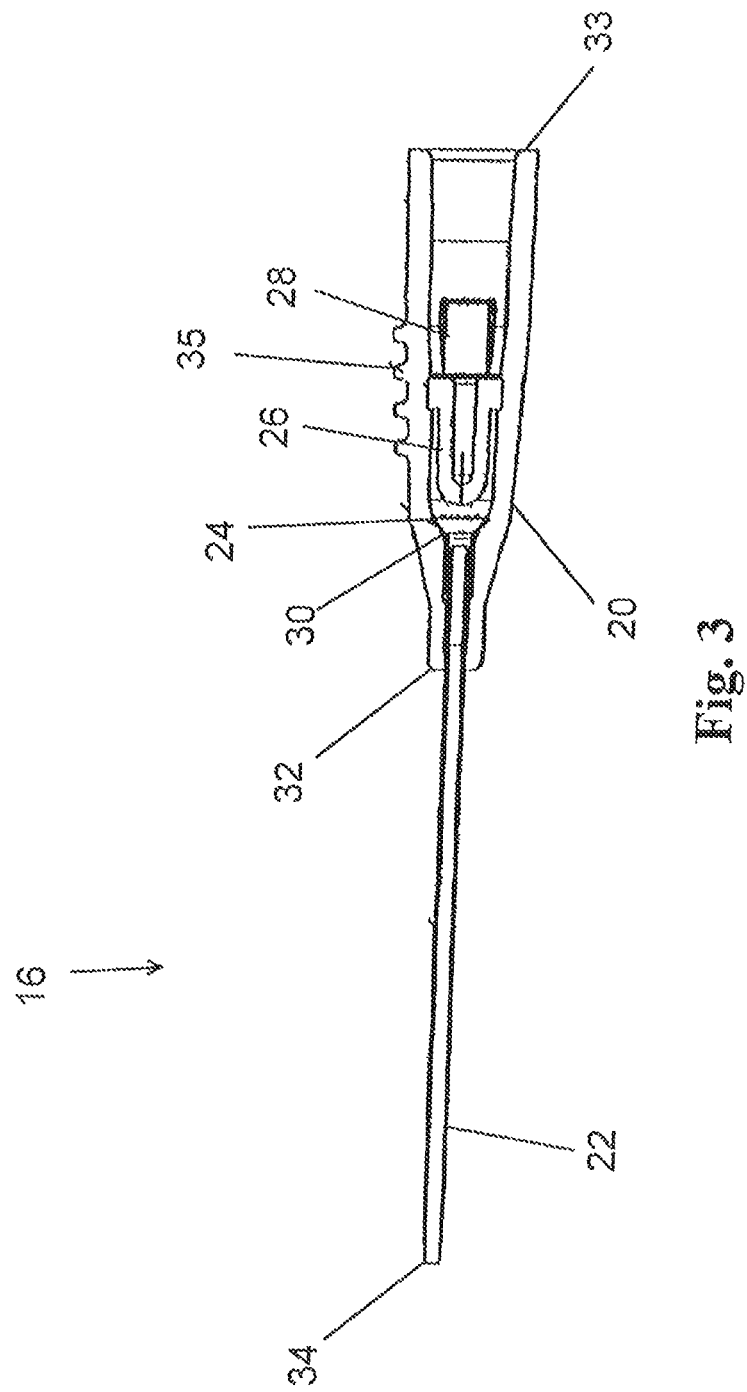
FIG. 3 is a side cross-section view of the luer assembly of the safety catheter shown in FIG. 2.

FIG. 3 illustrates a more detailed cross-section view of the luer assembly 16. In one version, the cannula 22 comprises a proximal end 30 and a distal end 34, where the proximal end 30 of the cannula 22 is bonded or otherwise attached to the eyelet 24. During assembly of the luer assembly 16, the eyelet 24, attached to the cannula 22, is fitted into the proximal end 33 of the hollow body portion 20 such that the cannula 22 extends from the distal end 32 of the body portion 20, as illustrated. After engaging the cannula 22 and eyelet 24 with the body portion 20, a one-way valve 26 may be positioned inside the hollow body portion 20 proximate the eyelet 24. The one-way valve, or other suitable blocking and/or selectively accessible component, allows for the stylet 36 of the shuttle assembly 50 (FIG. 4) to pass therethrough during operation of the safety catheter 10, but seals upon removal of the stylet 36 to prevent fluid from passing out of the luer assembly 16 until a proper attachment with a syringe, or the like, is created. In this manner, the luer assembly 16 can remain within the vasculature while various components are connected thereto via the one-way value for fluid delivery or removal.

The cannula 22 may be configured from any material, such as a flexible, bio-compatible elastomeric material, suitable for insertion into the vasculature of a patient. It will be appreciated that the cannula 22 may be transparent or semi-transparent to allow visualization of blood or other fluid, have any suitable internal diameter, have a bias toward a particular shape or configuration, be rigid or semi-rigid, and/or have any suitable geometry at the distal end 33 thereof. In an alternate version, the cannula 22 is integral with the eyelet 24 and/or one-way valve 26. It will be appreciated that the coupling of the components of the luer assembly 16 may be accomplished with any suitable engagement means such as with an adhesive, snap fit, friction fit, or the like.

Still referring to FIG. 3, the illustrated version of the hollow body portion 20 has a generally frustoconical shape tapering from the proximal end 33 to the distal end 32. The proximal end of the eyelet 24 is configured to initially accept the stylet 36 and the distal end 46 of the shuttle body 38 during engagement of the luer assembly 16 and shuttle assembly 50. The outer surface of the luer or hollow body portion 20 may include a textured surface 35, such as a knurled surface or ridged surface, configured to be gripped by a user during operation of the safety catheter 10. The illustrated version of the hollow body portion 20 further comprises a pair of guides 28 configured to engage resilient fingers 66 on the body portion 54. It will be appreciated that the hollow body portion 20 may have any suitable shape or configuration designed to retain a cannula 22, to be advanced distally by a user, and/or to engage resilient fingers 66 associated with the body portion 54. It will be appreciated that the hollow body portion 20 may include any suitable number of guides 28, such as one or a plurality of guides, configured to engage a corresponding one or a plurality of resilient fingers 66.

Figure 8:
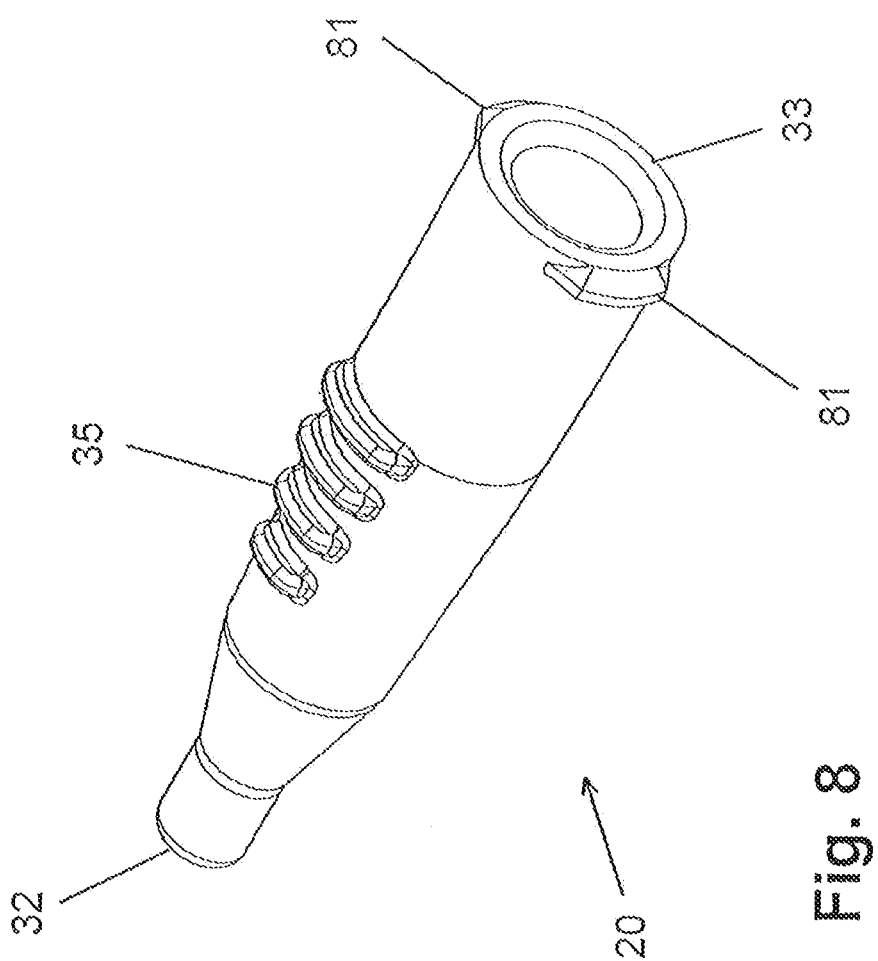
FIG. 8 is a perspective view of the luer or hollow outer portion shown in FIG. 2.

With reference to FIG. 1 and FIG. 8, the hollow body portion 20 further comprises a pair of lateral flanges 81 configured to engage the actuator 80 (FIG. 1), as will be described with more detail in reference to FIGS. 18-27a.

The luer assembly 16 is configured for removal from the safety catheter 10 and is designed to establish the site for fluid access into the vasculature of the patient. After the luer assembly has been properly positioned within a patient's vasculature, the other components of the safety catheter 10 will be removed such that an I.V. line, or the like, may be coupled with the luer assembly 16. It will be appreciated that the luer assembly 16 can include any suitable access means to the vasculature of a patient and/or means for coupling to a fluid delivery or extraction means.

Figure 4:
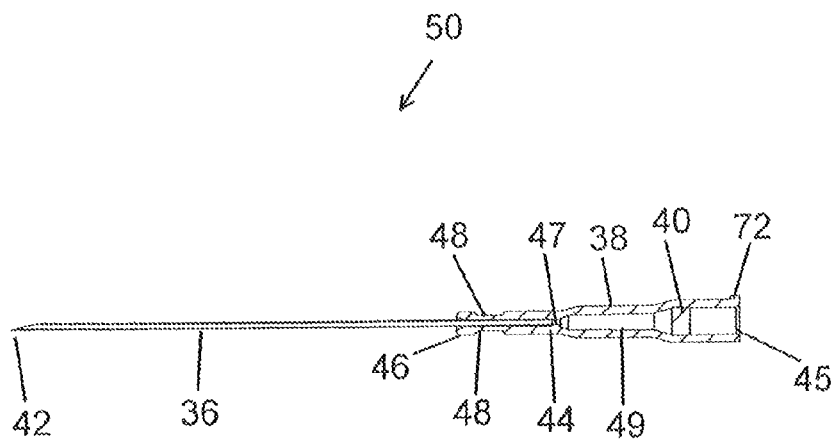
FIG. 4 is a side cross-section view of the shuttle assembly of the safety catheter shown in FIG. 2.

FIG. 4 illustrates a cross-section view of one version of the shuttle assembly 50 associated with safety catheter 10. The shuttle assembly 50 comprises a shuttle body 38 having a proximal end 45 and a distal end 46. In the illustrated version, the distal end 46 of the shuttle body 38 comprises a channel 47 configured to retain a needle or stylet 36 having a proximal end 44 and a distal end 42. The channel 47 extends proximally from the distal end 46 of the shuttle body 38 along a portion of the shuttle body 38 and may be configured to retain the stylet 36 in any suitable manner such as, for example, with an adhesive, a bonding, a friction fit, or any other suitable mechanical engagement. In one version, the stylet 36 is integral with the shuttle body 38. The proximal end 45 of the shuttle body 38 comprises a laterally projecting annular flange 72 where, as shown in more detail in FIGS. 18-27a, the spring 70 is retained between the annular flange 72 and an annular flange 61 on the body top 54.

In one version, the shuttle body 38 is configured from a transparent or semi-transparent material to facilitate the visualization of fluid, such as blood, therein. In one version, the shuttle body 38 further comprises a cavity 49 defined by the outer wall of the shuttle body 38, the proximal end of the channel 47, and the filter plug 40. The stylet 36, in one version, has a lumen therethrough to facilitate the flow of blood, or other fluid, from the distal tip 42 to the proximal end 46 and into the cavity 49. Fluid entering the cavity 49 is trapped by the filter plug 40. In one version, at least the portion of the shuttle body 38 defining the cavity 49 is transparent, where upon accessing a patient's vasculature, blood will pass through the stylet 36 lumen and into the cavity 49 such that a clinician can see that the vasculature was successfully accessed. The stylet 36 may have any suitable configuration, such as a beveled distal tip 42, to facilitate access to a patient's vasculature. The filter plug 40 is configured to prevent fluid from passing out of the shuttle body 38 and may be integral with the shuttle body or bonded to the shuttle body 38.

Figure 5:
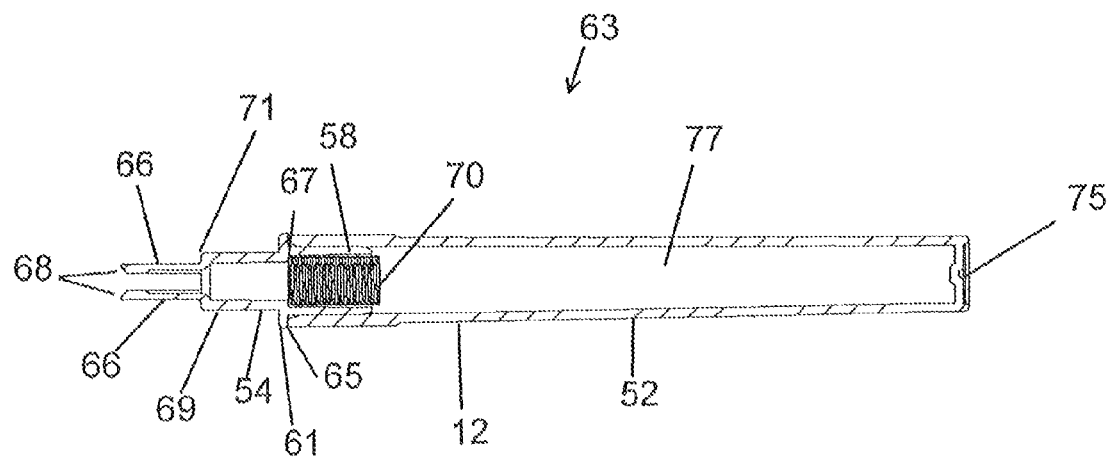
FIG. 5 is a side cross-section view of the holder assembly of the safety catheter shown in FIG. 2.

Still referring to FIG. 4, in the illustrated version, the shuttle body 38 comprises a pair of opposing indents or flats 48 at or near the distal end 46. The flats 48 are configured to engage a corresponding pair of projections 68 located on resilient arms 66 associated with the body portion 54 (FIG. 5). It will be appreciated that the shuttle body 38 may include any suitable number of flats 48, or other coupling feature, configured to engage any suitable number of resilient arms 66 and/or projections 68. It will be appreciated that the features of the illustrated components are provided by way of example only, where any components suitable for facilitating the operation of the device in accordance versions and methods described herein are contemplated.

During assembly of the luer assembly 16 (FIG. 3) and the shuttle assembly (FIG. 4), the distal tip 42 of the stylet 36 is inserted into the proximal end 33 of the hollow body portion 20, through the one way valve 26, and through the flexible cannula 22. In this manner, the stylet 36 operates to stiffen the cannula 22 such that it can be inserted into the vasculature of the patient. The outer diameter of the stylet 36 may configured to be approximately the same as the inner diameter of the cannula 22 such that a seal is created between the cannula 22 and stylet 36, however, any suitable relationship between the cannula 22 and stylet 36 is contemplated. The stylet 36 may be inserted through the cannula 22 until the distal end 46 of the shuttle body abuts or nears the proximal end of the one way valve 26. The safety catheter 10 may include a cannula 22 and stylet 36 of any suitable length. In one version, the cannula 22 has a length that is approximately a centimeter shorter than the length of the exposed stylet 36 when initially engaged with the hollow body portion 20, however, any suitable dimension and relationship is contemplated.

Generally, the shuttle assembly 50 is configured to provide sufficient rigidity to the cannula 22 of the luer assembly 16 until the luer assembly 16 is properly positioned. Once positioned, as shown in more detail with reference to FIGS. 18-27a, the luer assembly 16 is removed from the shuttle assembly by initially advancing the luer assembly 16 with an actuator 80 and then manually removing the luer assembly 16 completely from the rest of the safety catheter 10. Once the shuttle assembly 50 is removed, the cannula 22 may regain its flexibility and the lumen of the cannula 22 will be clear for the transfer of fluid therethrough.

Referring to FIG. 5, one version of a handle assembly 63 is illustrated comprising a handle body 52, a body top 54, an actuator 80 (FIG. 17), and a spring 70. In the illustrated version, the body top 54 has a generally cylindrical proximal end 58 that is configured to be inserted into and bonded with the distal end 59 of the handle body 52. The body top 54 comprises an annular flange 61 having an outer portion 65 that abuts the distal end 59 of the handle body when engaged. The body top 54 and handle body 52 may have any suitable coupling including a bonding, a snap fit, a friction fit or, in an alternative embodiment, can be configured as an integral structure. The annular flange 61 of the body top 54 further comprises an inner portion 67 configured to retain a spring 70 within the handle body 52 in combination with the shuttle body 38 of the shuttle assembly 50 (shown in FIGS. 18-27a). More specifically, when the safety catheter 10 is assembled, the spring 70 is positioned between the annular flange 72 on the shuttle body 38 (FIG. 4) and the inner portion 67 of the annular flange 61. In one version, the spring 70 is used to selectively provide a motive force that is configured to translate the shuttle assembly 50 relative to the handle assembly 63 during operation.

Figure 9:
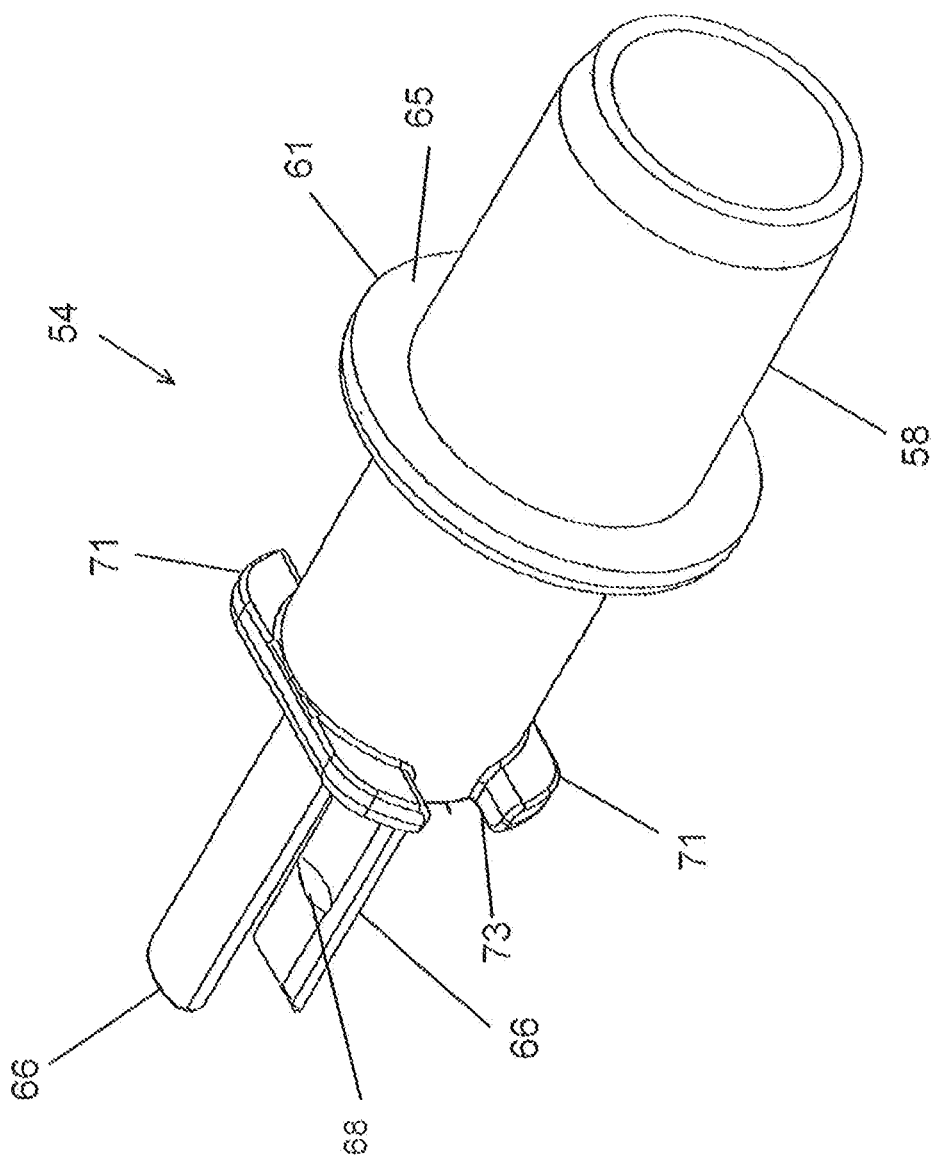
FIG. 9 is a perspective view of the body top shown in FIG. 2.

Referring to FIG. 9, a distal end 69 of the body top 54 comprises a pair of stops 71 projecting laterally outward from the body top 54. The stops 71 define a pair of gaps 73 (FIG. 2) therebetween. An actuator 80 is configured to engage the distal end 69 of the body top 54 and is configured to translate axially relative thereto. The operation of the actuator 80 relative to the body top 54 will be described in more detail with reference to FIGS. 17-27a. Projecting proximally from the distal end 69 of the body top 54 are a pair of resilient arms 66 having projections 68 projecting laterally inward from the distal ends thereof. The resilient arms 66, in the illustrated version, are configured to pivot as a living hinge about the connection point between the resilient arms 66 and the distal end 69 of the body top 54. The projections 68 are configured to engage the flats 48 on the shuttle body 38 of the shuttle assembly 50 as will be described in more detail with reference to FIGS. 18-27a.

Figure 21:
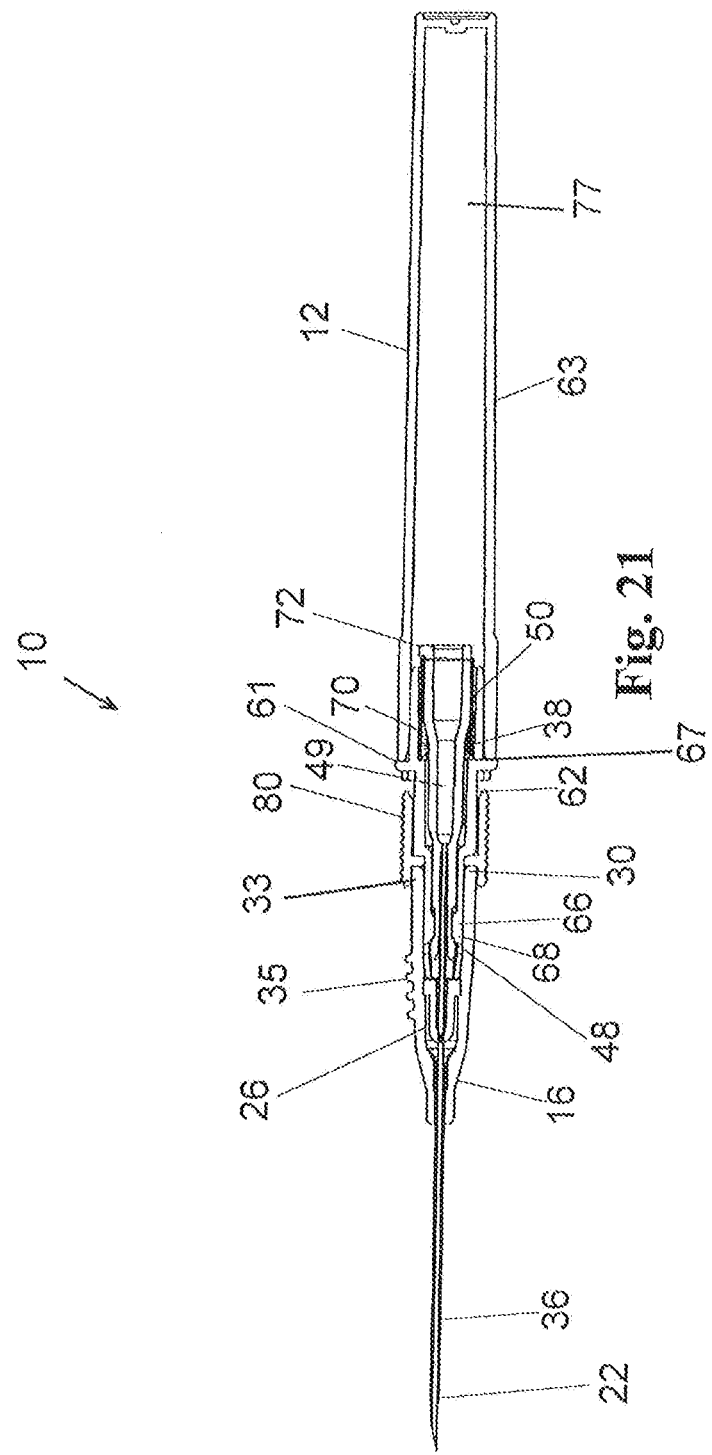
FIG. 21 is a side cross-section view of the safety catheter of FIG. 20, shown rotated ninety degrees.
Figure 21A:
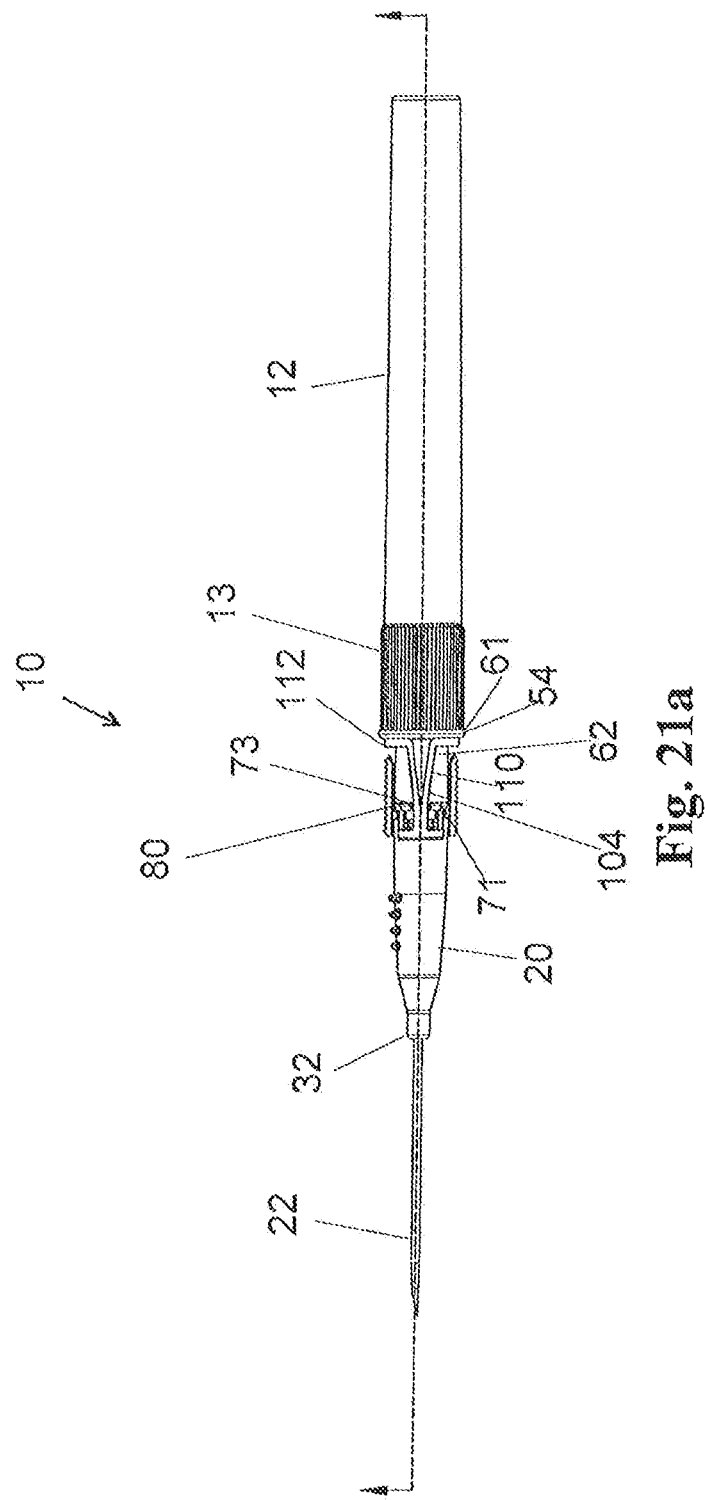
FIG. 21a is a side view of the safety catheter of FIG. 20.

Still referring to FIG. 5, one version of the body top 54 comprises providing a least a portion of the body top 54 that is transparent or semi-transparent. In one version, when the handle assembly 63 is engaged with the shuttle assembly 50, as will be described in more detail herein, the cavity 49 of the shuttle body 38 is aligned with the distal portion of the body top 54. With reference to FIGS. 20-21a, by providing a transparent distal portion 69 of the body top 54, which aligns with the transparent portion of the shuttle body 38 covering the cavity 49, a flash window 62 is created that allows a clinician to see that a patient's vasculature has been properly accessed. Providing a flash window 62 may eliminate a clinician having to guess as to the proper placement of the safety catheter 10 within the patient. After access to the vasculature has been confirmed, the safety catheter 10 may be further operated in accordance with FIGS. 18-27a. It will be appreciated that the luer assembly 16, the shuttle assembly 50, and the handle assembly 63 are described by way of example only, where any suitable components in any suitable configuration may be provided in accordance with versions described herein. Components may be separate or integral.

Figure 10:
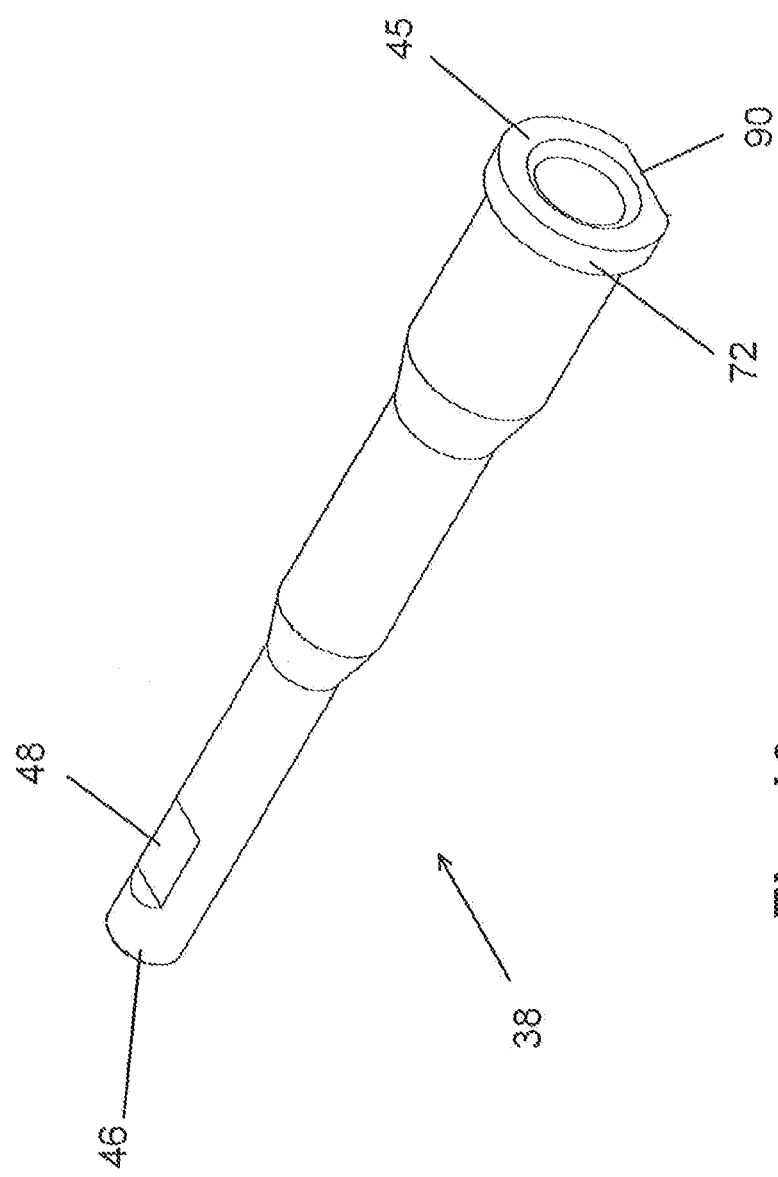
FIG. 10 is a perspective view of the shuttle body shown in FIG. 2.
Figure 11:
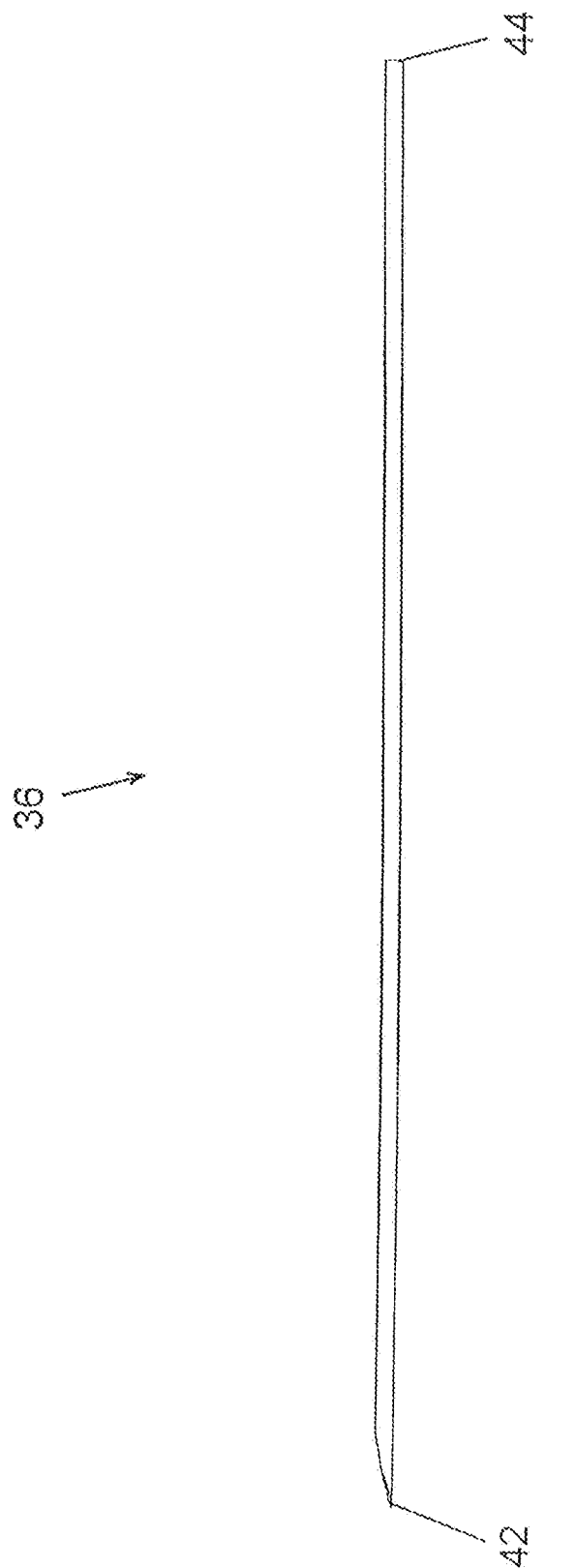
FIG. 11 is a side view of the stylet shown in FIG. 2.
Figure 12:
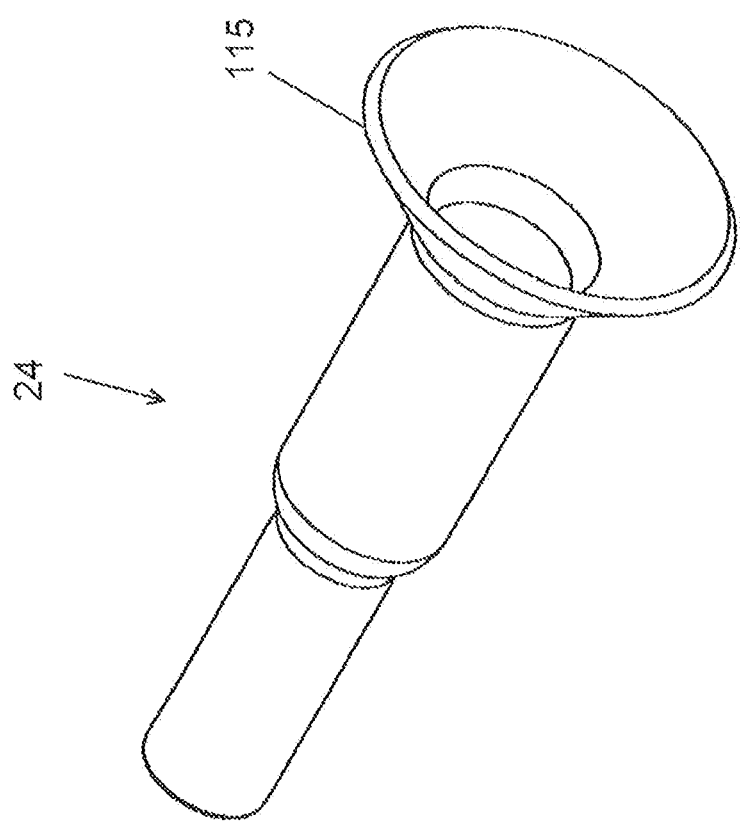
FIG. 12 is a perspective view of the eyelet shown in FIG. 2.
Figure 13:
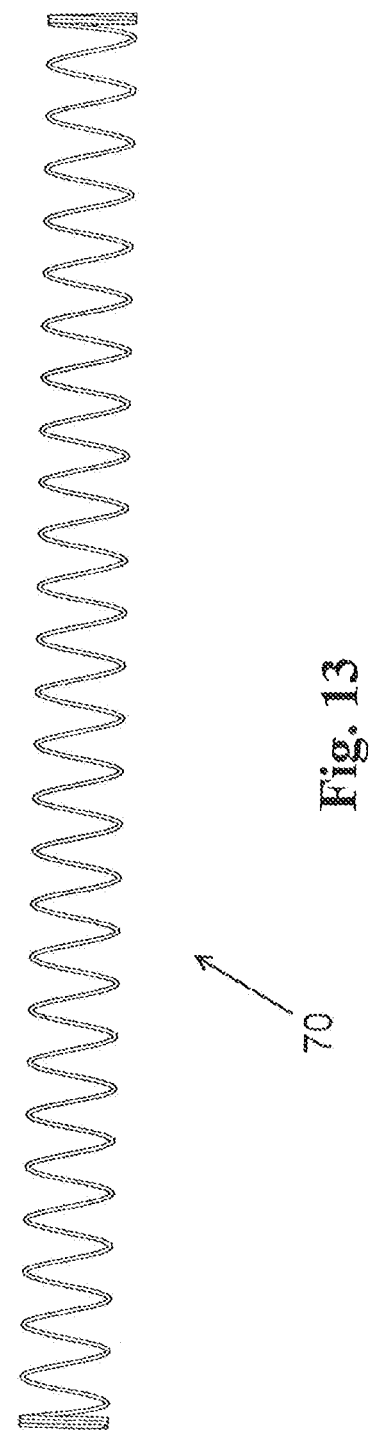
FIG. 13 is a perspective view of the spring shown in FIG. 2.
Figure 14:
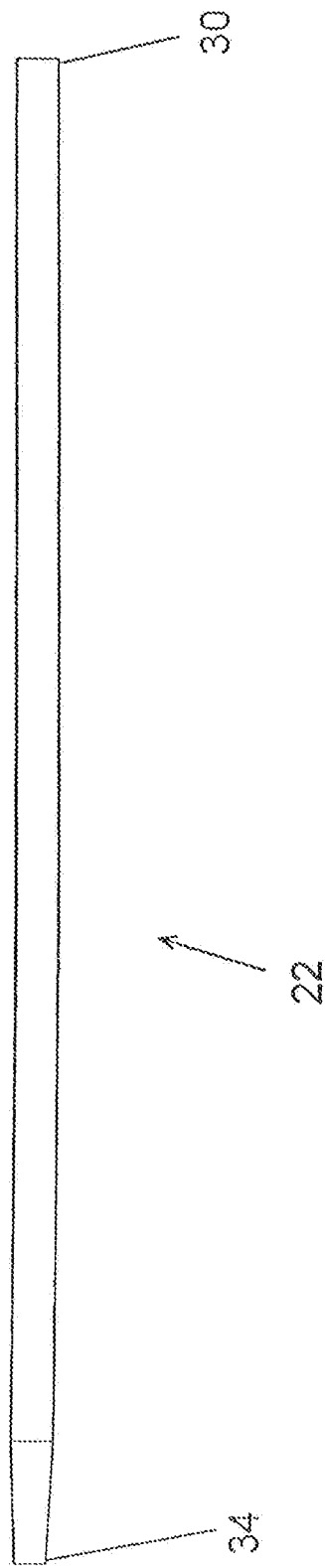
FIG. 14 is a side view of the catheter shown in FIG. 2.
Figure 15:
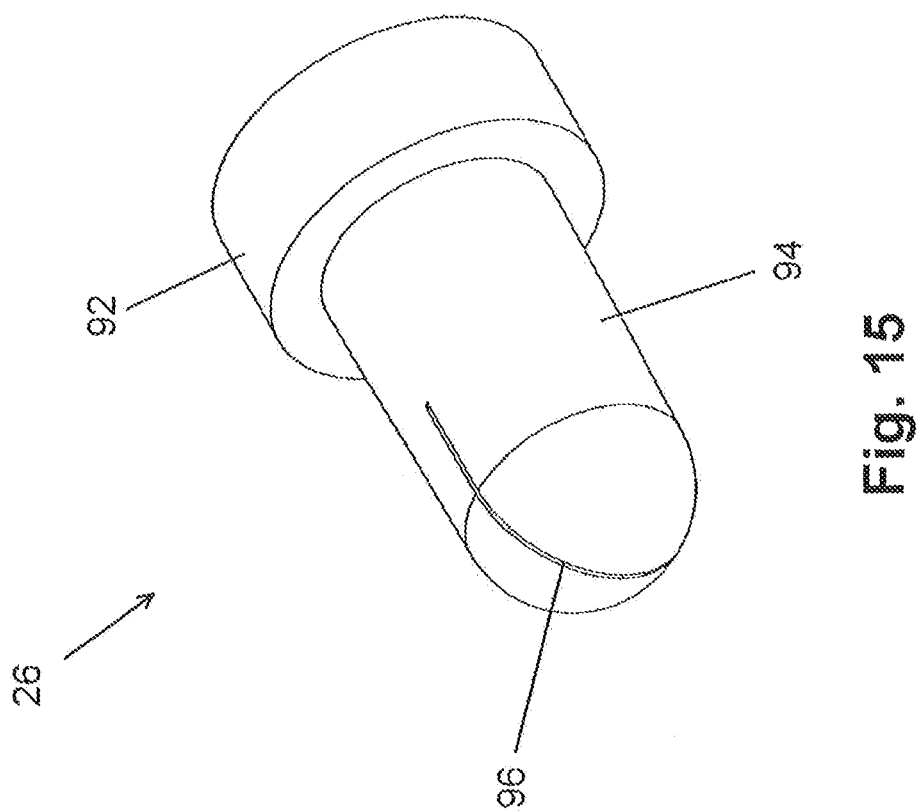
FIG. 15 is a perspective view of the one-way valve shown in FIG. 2.
Figure 16:
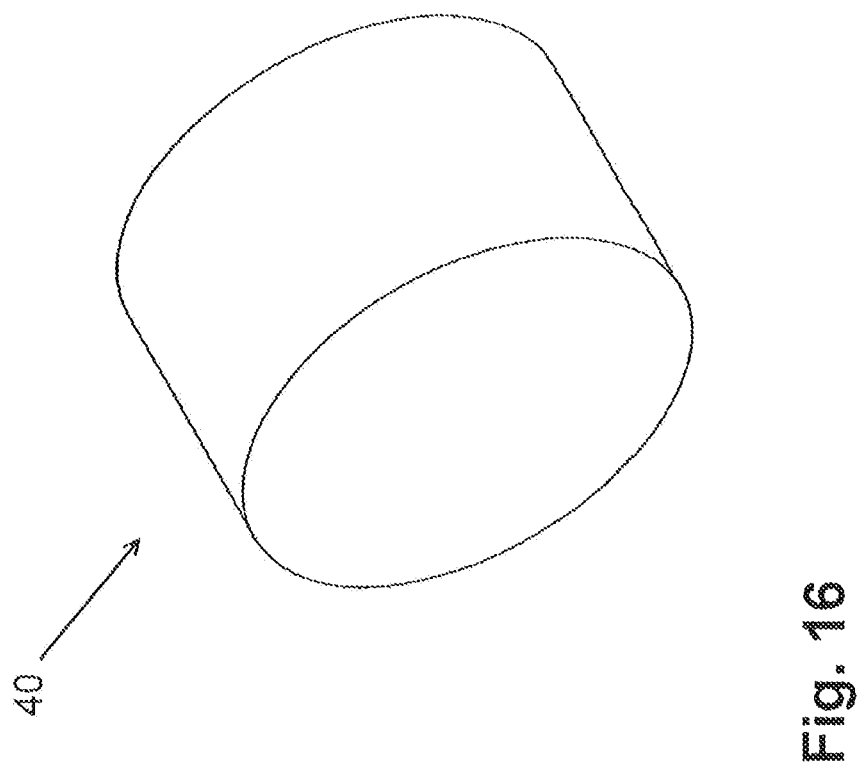
FIG. 16 is a perspective view of the filter or stop shown in FIG. 2.

FIG. 6 illustrates a more detailed perspective view of the shield 14 and FIG. 7 illustrates a more detailed perspective view of the handle 12. FIG. 8 illustrates a more detailed perspective view of the hollow body portion 20. FIG. 9 illustrates a more detailed perspective view of the body top 54. FIG. 10 illustrates a more detailed perspective view of the shuttle body 38, where in one version the shuttle body 38 comprises a flat 90. FIG. 11 illustrates a more detailed side view of the stylet 36. FIG. 12 illustrates a more detailed perspective view of the eyelet 24 having, in one version a conical bevel 115. FIG. 13 illustrates a more detailed side view of the spring 70. FIG. 14 illustrates a side view of cannula 22, where in one version the cannula 22 comprises a distal end 34 having a taper. FIG. 15 illustrates a more detailed perspective view of the one-way valve 26. The one-way valve may be any suitable valve and may include, for example, an annular collar 92 and a distal valve portion 94 having a slit 96 therein. The valve portion 94 may be configured from any suitable material such that the slit 96 is normally sealed unless penetrated, for example, by the stylet 36 or other vasculature access or delivery device or componet. It will be appreciated that any suitable valve or component that selectively restricts the movement of fluid is contemplated. FIG. 16 illustrates a more detailed perspective view of the filter plug 40. It will be appreciated that filter plug 40 may be configured from any suitable material and may have any suitable configuration to prevent or obstruct the flow of fluid while allowing displacement of air or another gas.

FIG. 17 illustrates one version of an actuator 80 having a proximal end 98 and a distal end 100. Actuator 80 comprises a base 95 having a dorsal thumb pad 97, a pair of distally extending rails 102, and a pair of lateral arms 104. The lateral arms 104 further comprise a pair of distal retention latches 106 having inwardly projecting lateral projections 108 and a pair of proximal living hinges 110. The proximal ends of the living hinges 110 are joined by a pair of crescent-shaped bands 112 that form a partial annular band at the proximal end of the actuator 80. The operation of actuator 80 will be described in more detail with reference to FIGS. 18-27a.

With reference to FIGS. 18-27a, one version of the operation of the safety catheter 10 is illustrated. Generally, the operation of the safety catheter is to transition the shuttle assembly 50 from a first position distal to the handle 12 to a second location inside the chamber 77 of the handle 12. More specifically, in one version, when the shuttle assembly 50 in its first location on the handle 12, the safety catheter 10 can be used to establish fluid access for the luer assembly 16 into the vasculature of the patient. To maintain this fluid access site, the luer assembly 16 is separated from the rest of the safety catheter 10. After separating the luer assembly 16 from the rest of the safety catheter 10, the shuttle assembly 50 is retracted to its second location inside the handle 12. When in the second position, the sharp distal tip 42 of the stylet 36 is effectively concealed inside the chamber 77 of the handle 12 to prevent inadvertent or accidental "sticks" by the stylet 36.

Figure 19A:
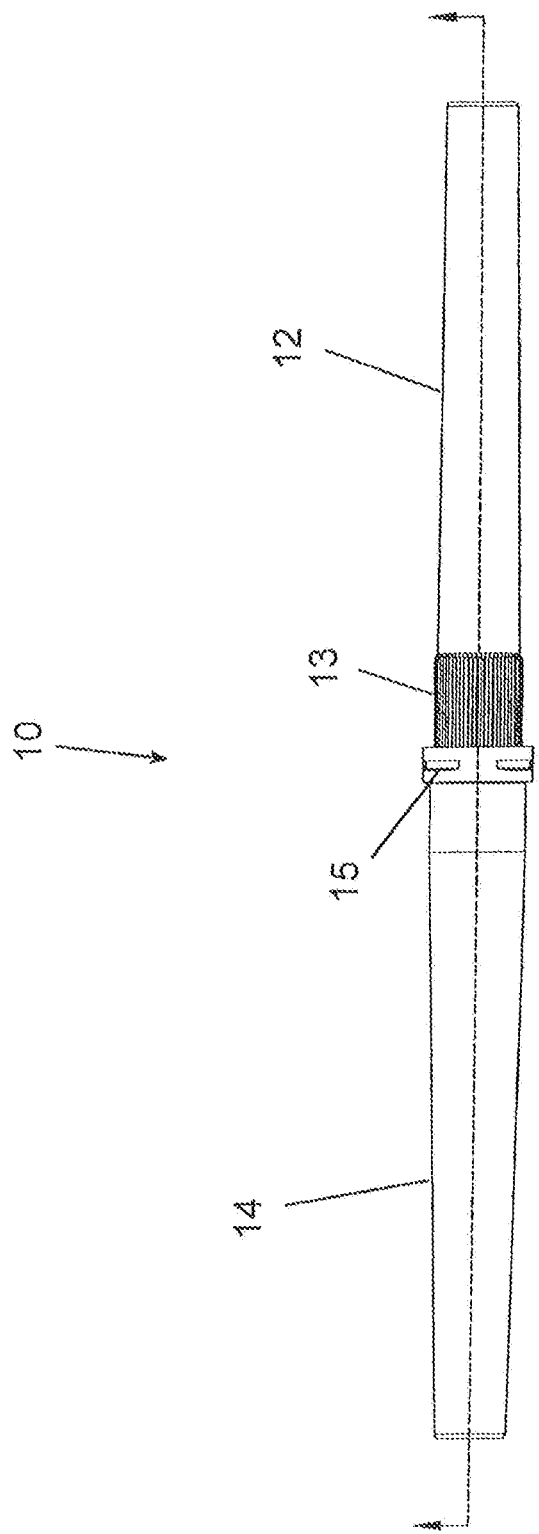
FIG. 19a is a side view of the safety catheter of FIG. 19.

Referring FIGS. 18-19a, the safety catheter 10 is shown in it pre-use configuration with the shield 14 engaged with the handle 12 to effectively conceal the stylet 36. The safety catheter 10 may be packaged in any suitable manner for the safe transport and/or storage on the device.

FIGS. 20-21a illustrate one version of the safety catheter 10 after removal of the shield 14 therefrom such that the safety catheter 10 is in a configuration designed to access the vasculature of a patient. When the shuttle assembly 50 is in its first location, the luer assembly 16, the shuttle assembly 50 and the handle assembly 63 all interact with each other. As illustrated, the stylet 36 of the shuttle assembly 50 is retained within the cannula 22 of the luer assembly 16 and the distal end 46 of the shuttle body 38 is positioned proximal to and adjacent the one-way valve 26 of the luer assembly 16 within the guides 28. The stylet 36 extends distally from the shuttle body 38, through the one-way valve 26, and through the cannula 22. In the illustrated configuration, the stylet 36 stiffens the cannula 22 for insertion into the vasculature of a patient.

At the same time, the proximal end 33 of the hollow body portion 20 of the luer assembly 16 is positioned over the resilient fingers 66 of the body top 54, where the projections 68 on the resilient fingers are engaged, as best seen in FIG. 21, with the flats 48 of the shuttle body 38. As illustrated in FIGS. 20 and 21, positioning the hollow body portion over the resilient arms 66 maintains the projections 68 within the flats 48 such that the shuttle assembly 50 is unable to move relative to the handle assembly 63. This interaction between the luer assembly 16, the shuttle assembly 50, and the handle assembly 63 effectively holds the shuttle assembly 50 in its first location relative to the handle 12. While the shuttle assembly 50 is in its first location, as shown in FIGS. 20-21a, the spring 70 is compressed between the annular flange 72 on the shuttle body 38 and the annular flange 61 on body top 54. The spring 70 is configured to bias the shuttle assembly 50 proximally into the holder 12, however, the retention of the projections 68 of the resilient arms 66 within the flats 48 prevents the proximal retraction of the shuttle assembly 50. The spring 70 will remain compressed until the shuttle assembly is released from both the luer assembly 16 and the actuator 80.

Still referring to FIGS. 20-21a, the actuator 80 is shown engaged with the body top 54 and with the proximal end 33 of the hollow body portion 20 of the luer assembly 16. More specifically, in the illustrated version, the retention latches 106, having lateral projections 108, are engaged with the lateral flanges 81 on the hollow body portion 20. In this configuration, the luer assembly 16 is secured to the rest of the safety catheter 10. As best seen in FIG. 21a, the neck of the lateral arms 104 is positioned in the gaps 73 between the stops 71 on the body top 54. The bands 112 of the actuator substantially encircle the distal end of the body top 54 adjacent the annular band 61. In this position, the actuator 80 is secured to the body top 54 and the living hinges 110 of the lateral arms 104 are in a relaxed position, where only the necks of the lateral arms 104 are positioned within the gaps 73 between the stops 71 of the body top 54.

As shown in FIGS. 20-21a, the safety catheter is configured for insertion into the vasculature of a patient. Upon insertion of the cannula 22 and stylet 36 into the patient, versions herein comprise confirming that the safety catheter 10 has been properly positioned such that the luer assembly 16 is in fluid communication with the vasculature of the patient. After successfully accessing the vasculature, blood will pass through the lumen of the stylet 36 and into the cavity 49 within the shuttle body 38. Because, in one version, the shuttle body 38 and surrounding body top 54 are transparent, the blood will be visible through this flash window. Visualizing blood through the flash window 62 will indicate to the clinician that the vasculature has been properly accessed. The filter plug 40 confines the blood that enters into the cavity 49 of the shuttle assembly 50 and prevents blood born pathogens from leaking out of the safety catheter 10.

Figure 22:
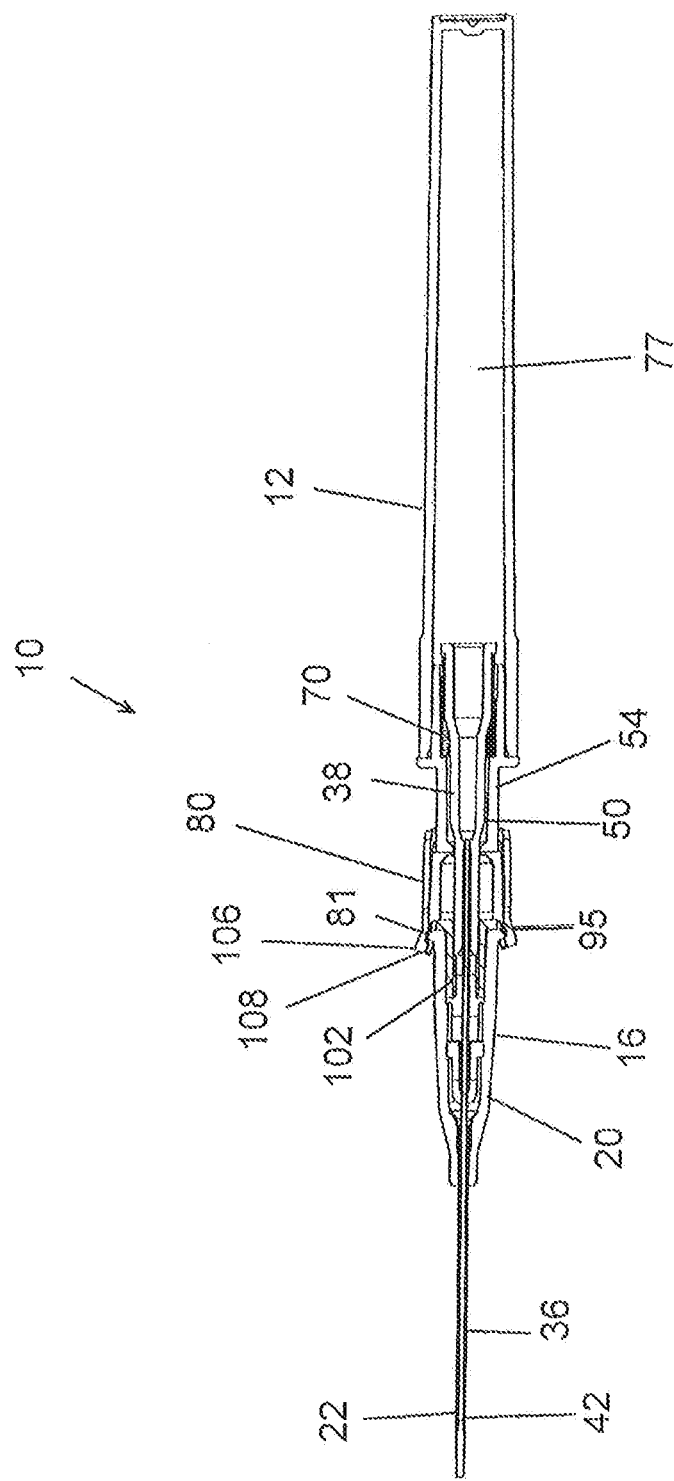
FIG. 22 is a side cross-section view of the safety catheter of FIG. 1, shown with the actuator and the luer assembly distally advanced.
Figure 23:
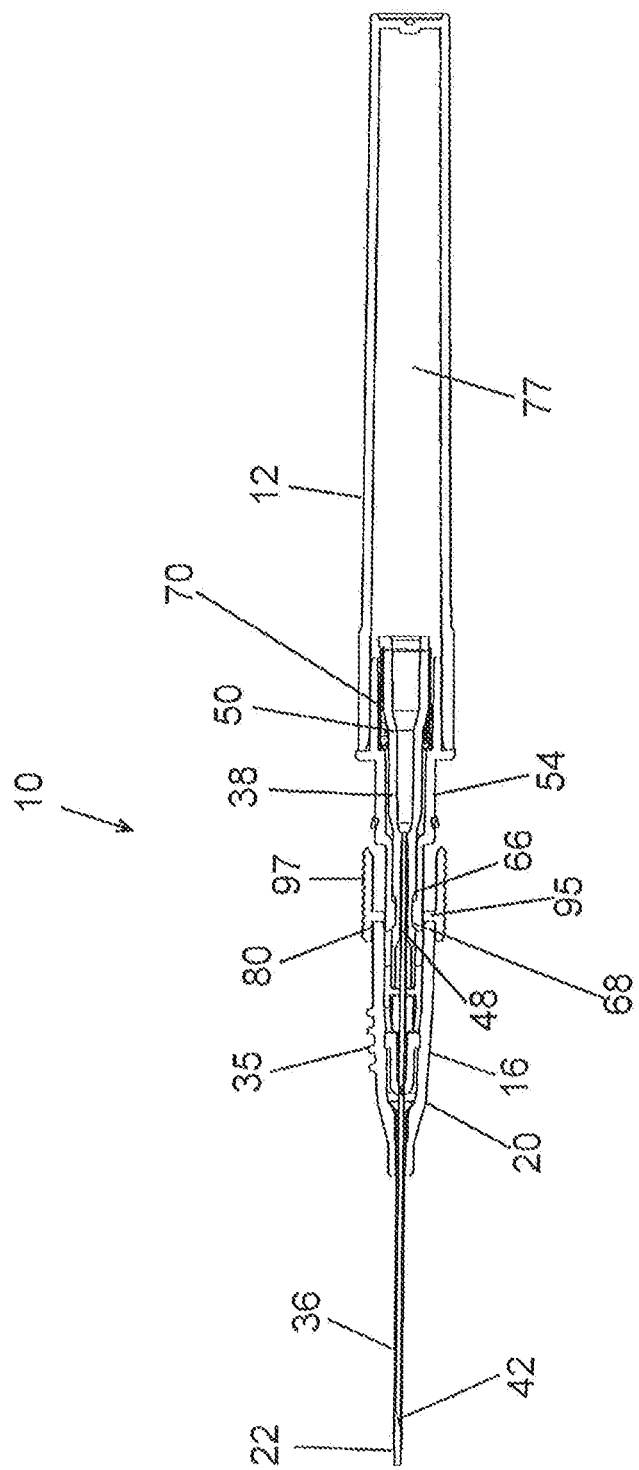
FIG. 23 is a side cross-section view of the safety catheter of FIG. 22, shown rotated ninety degrees.
Figure 23A:
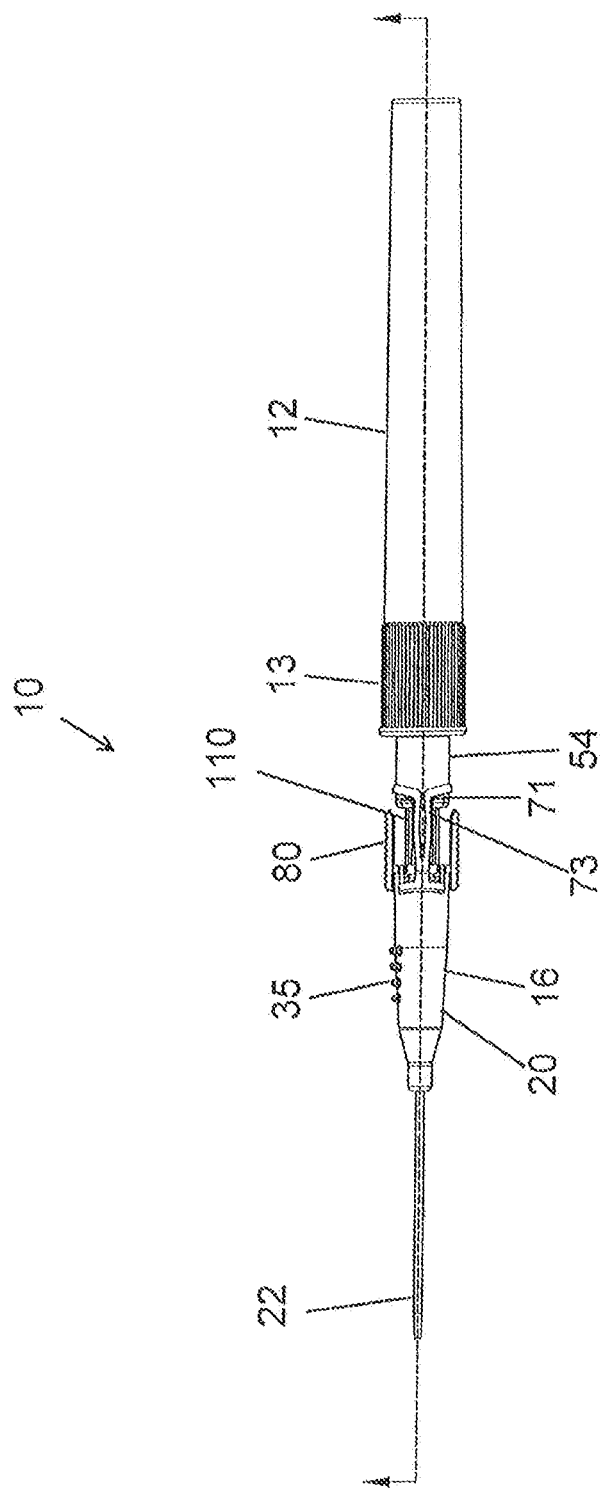
FIG. 23a is a side view of the safety catheter of FIG. 23.

With reference to FIGS. 22-23a, after the vasculature of a patient has been accessed, the cannula 22 can be advanced beyond the distal tip 42 of the stylet 36 and/or farther into the vasculature. Advancing the cannula 22 is accomplished by the clinician placing, for example, their index finger on the dorsal pad 97 (FIGS. 23-23a) and distally advancing the actuator. As the actuator 80 is advanced, the retention latches 106 flex outward to disengage the lateral projections 108 from the lateral flanges 81 on the hollow body portion 20 of the luer assembly 16. This disengagement frees the luer assembly 16 for removal from the rest of the safety catheter 10. Concurrently, as the actuator 80 is advanced, the rails 102 push the luer assembly 16 distally, thus advancing the cannula 22 farther into the vascular of the patient. As the luer assembly 16 is pushed distally by the actuator 80, the base 95 of the actuator moves to cover the resilient arms 66 (FIG. 23) of the body top 54 such that the projections 68 are still retained within the flats 48 on the shuttle body 38. In this position, the hollow body portion 20 of the luer assembly 16 is no longer retaining the resilient arms, however, the actuator 80 prevents the resilient arms from expanding laterally to release and allow retraction of the shuttle assembly 50. In this manner the cannula 22 is extended further into the vasculature of a patient before allowing for the release of shuttle assembly. This configuration may be beneficial as it allows the cannula 22 to be advanced with some stiffness, and to be repositioned if necessary, before the stylet 36 is retracted into the handle 12. As the actuator 80 is advanced, the living hinges 110 (FIG. 23*a*) on the actuator are drawn and contracted through the gaps 73 between the stops 71 of the body top 54. This contraction biases the actuator 80 in a proximal direction, which upon release of the actuator, or by decreasing distal force on the actuator, will move the actuator proximally.

Figure 24:
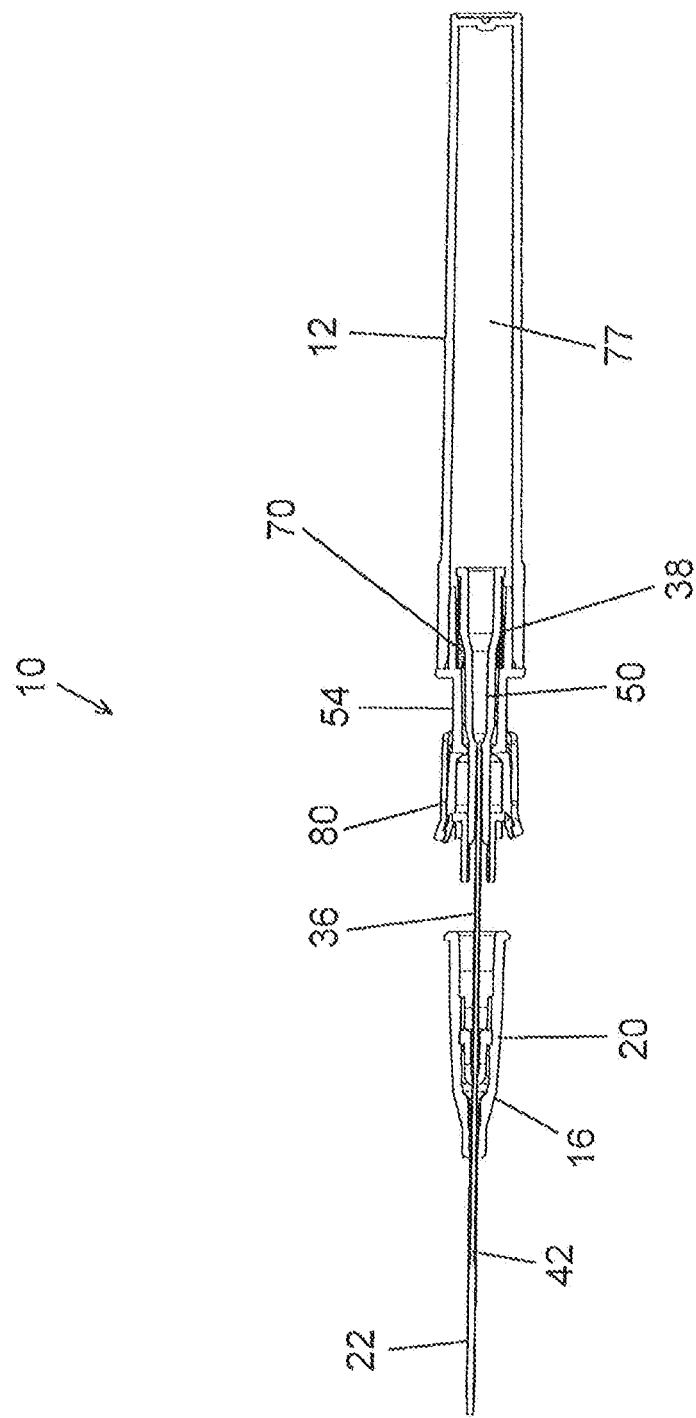
FIG. 24 is a side cross-section view of the safety catheter of FIG. 1, shown with the luer assembly disengaged from the shuttle assembly and handle assembly.
Figure 25:
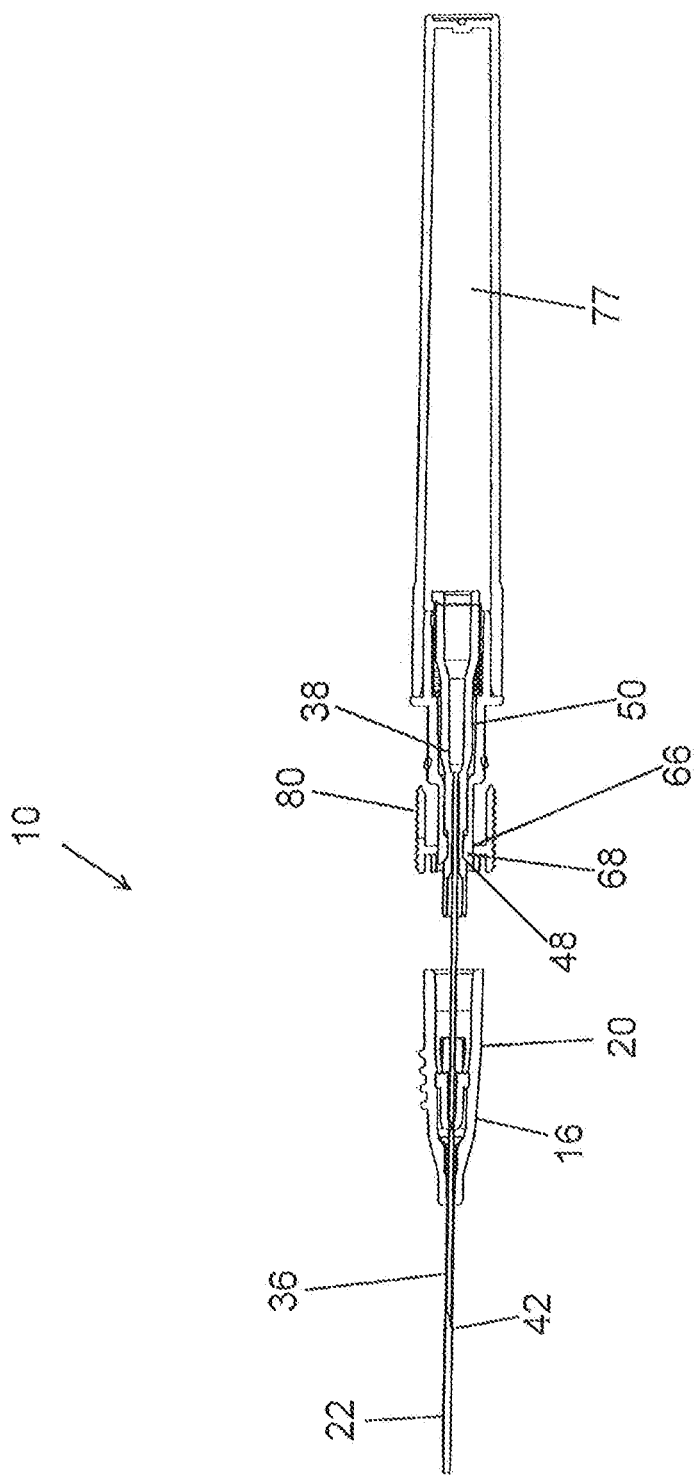
FIG. 25 is a side cross-section view of the safety catheter of FIG. 24, shown rotated ninety degrees.
Figure 25A:
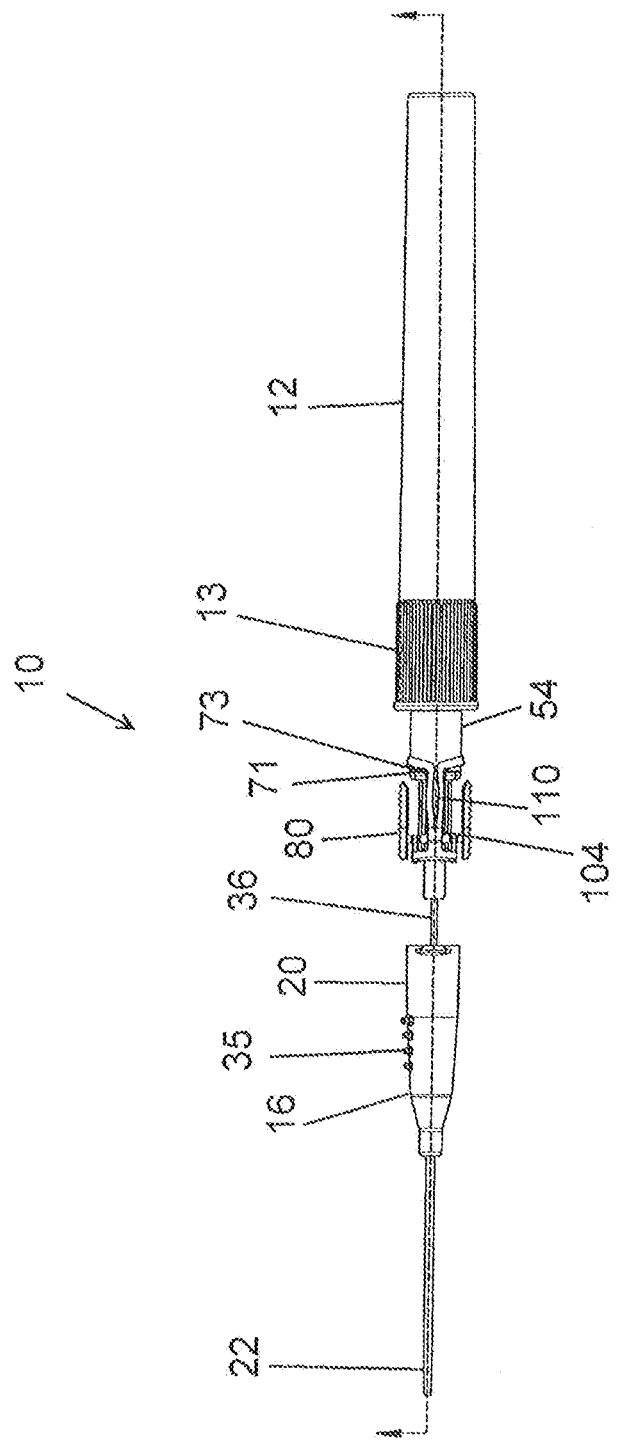
FIG. 25a is a side view of the safety catheter of FIG. 25.

With reference to FIGS. 24-25*a*, after the cannula 22 has been further advanced, the luer assembly 16 can removed from the rest of the safety catheter 10 and remain within the vasculature of a patient. With the clinician's finger still positioned on the actuator 80, retaining the stylet 36 and shuttle assembly 50 in the first position, the luer assembly 16 may be guided off the stylet 36. As illustrated, the actuator 80 (FIG. 25) will maintain the projections 68 of the resilient arms 66 within the flats 48 until the actuator 80 is allowed to retract, thereby securing the shuttle assembly in the first position until release of the stylet is desired.

Figure 27:
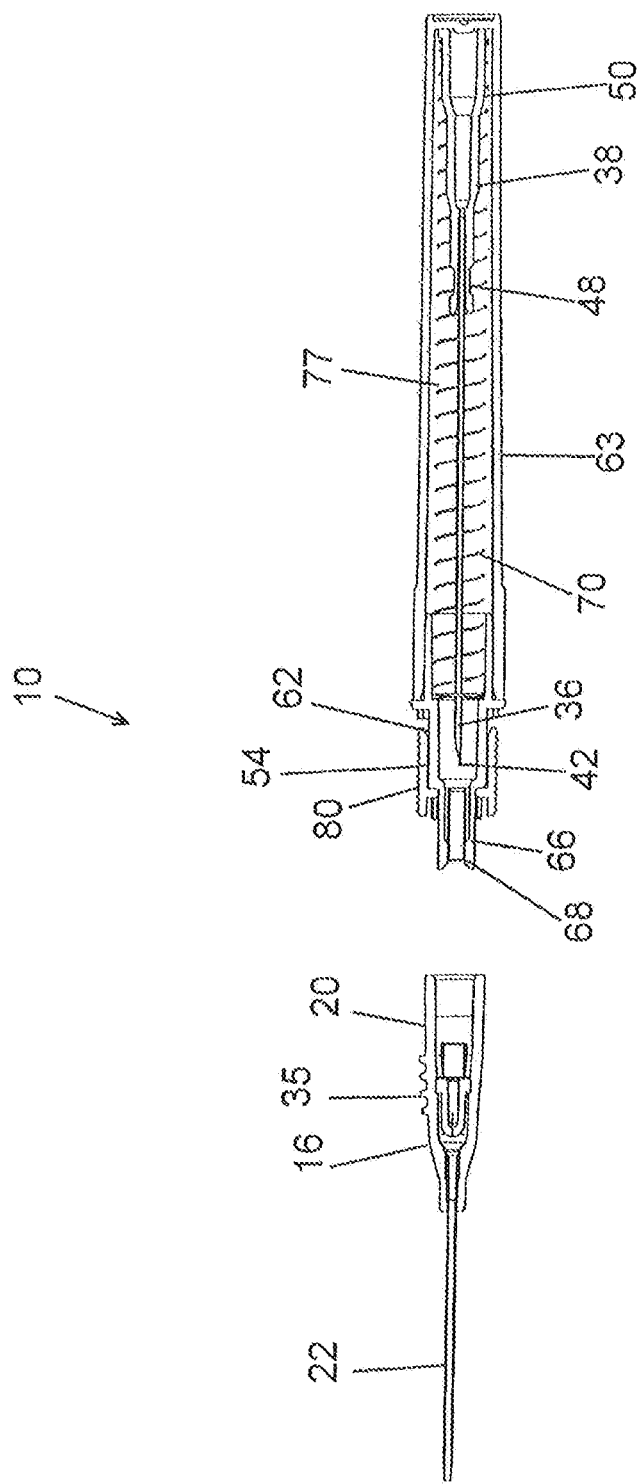
FIG. 27 is a side cross-section view of the safety catheter of FIG. 26, shown rotated ninety degrees.
Figure 27A:
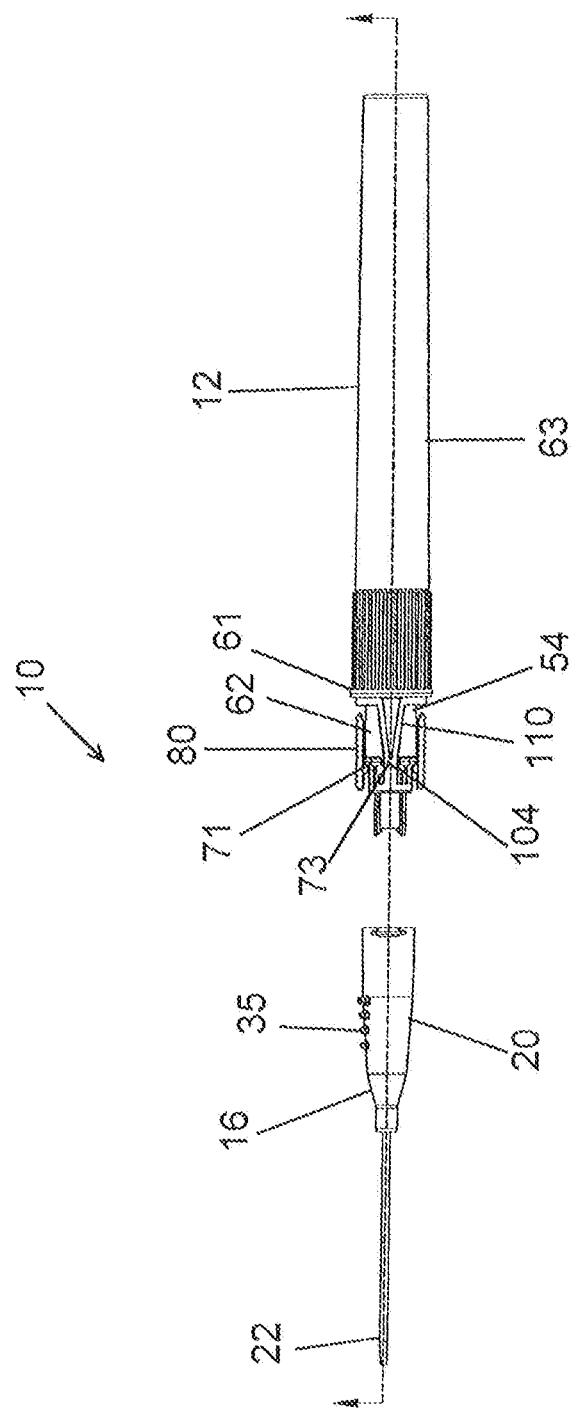
FIG. 27a is side view of the safety catheter of FIG. 27.

With reference to FIGS. 26-27*a*, the shuttle assembly 50 can be released for retraction into the handle 12 at any time after the luer assembly 16 has advanced. The luer assembly 16 can be partially or fully removed from the shuttle assembly 50 before allowing the shuttle assembly 50 to retract. Retraction is caused by the clinician releasing distal pressure on the actuator 80 such that the proximal bias of the living hinges 110 (FIG. 27*a*) urges the actuator proximally. As the actuator 80 moves proximally, the resilient arms 66 (FIG. 27), which are biased outwardly, are no longer retained within the flats 48. Once the resilient arms 66 are able to expand laterally, the projections 68 on the resilient arms disengage the flats 48. The shuttle body 38 of the shuttle assembly 50, once disengaged from the holder assembly 63, is urged to move proximally by the spring 70 retained within the handle 12. The spring 70 will urge the shuttle assembly 50 proximally into the chamber 77 of the handle 12, thus concealing the distal tip 42 of the stylet inside the handle 12. Concealing the stylet 36 in this manner can reduce the risks associated with accidental needle sticks. Once the shuttle assembly 50 is retained within the handle 12, in one version, the distal tip 42 of the stylet will be aligned with the flash window 62 on the body top 54. In this version, the clinician will be able to see the distal tip 42 and know that the stylet 36 is properly retained and no longer presents a risk.

It will be appreciated that the method of operating the safety catheter 10 is disclosed by way of example only, where steps may be provided in any suitable order with any suitable configuration of components to provide for controlled retraction, a flash window to view when the vasculature of patient has been accessed, and/or a flash window to view when a needle or stylet has been retracted to a safe position.

What is claimed is:

1. A safety catheter for use with a patient which comprises:
an elongated handle defining an axis and having a proximal end and a distal end, wherein the handle is formed with an internal chamber and has a plurality of resilient fingers extending parallel to the axis in a distal direction from the handle;
a luer assembly for establishing a site for fluid access into the vasculature of the patient;
a shuttle assembly, wherein the shuttle assembly is mounted for axial movement on the handle from a first location to a second location, with the luer assembly fitted onto the handle to urge the fingers thereof against the shuttle assembly to hold the shuttle assembly at the first location; and
an actuator mounted on the handle for movement between a proximal position and a distal position, wherein the actuator is formed with a base member having a plurality of rails extending distally therefrom and having at least one living hinge positioned outwardly therefrom, wherein during a forced movement of the actuator from its proximal position to its distal position, the base member holds the fingers of the handle against the shuttle assembly and the living hinge is compressed to bias the actuator for a return back toward its proximal position, and the rails push on the luer assembly to separate the luer assembly from the shuttle assembly, and wherein upon removal of the force from the actuator, the living hinge returns the actuator back to its proximal position to remove the base member from the fingers and to release the fingers of the handle from the shuttle assembly to separate the handle and the shuttle assembly from the luer assembly for retracting the shuttle assembly to its second location inside the chamber.

2. A safety catheter as recited in claim 1 wherein the base member overides the resilient fingers of the handle when the actuator is moved from its proximal position to its distal position.

3. A safety catheter as recited in claim 1 wherein the living hinge includes a pair of arms, and wherein the bias of the living hinge is created when the arms are forced toward each other during a movement of the actuator toward its distal position.

4. A safety catheter as recited in claim 1 further comprising a pad mounted on the base member for moving the actuator from its proximal position to its distal position.

5. A safety catheter as recited in claim 1 further comprising a spring for biasing the shuttle assembly into the internal chamber of the handle.

6. A safety catheter as recited in claim 5 wherein the spring is compressed between the shuttle assembly and the handle when the actuator is in the distal position.

* * * * *